United States Patent
De Pietri Tonelli et al.

(10) Patent No.: US 10,792,298 B2
(45) Date of Patent: Oct. 6, 2020

(54) MIRNA PHARMACEUTICAL COMPOSITIONS AND THERAPEUTIC USES THEREOF

(71) Applicant: FONDAZIONE ISTITUTO ITALIANO DI TECNOLOGIA, Genoa (IT)

(72) Inventors: Davide De Pietri Tonelli, Arenzano (IT); Meritxell Pons Espinal, Genoa (IT)

(73) Assignee: FONDAZIONE ISTITUTO ITALIANO DI TECNOLOGIA, Genoa (IT)

(*) Notice: Subject to any disclaimer, the term of this patent is extended or adjusted under 35 U.S.C. 154(b) by 22 days.

(21) Appl. No.: 16/331,546

(22) PCT Filed: Sep. 18, 2017

(86) PCT No.: PCT/IB2017/055617
§ 371 (c)(1),
(2) Date: Mar. 8, 2019

(87) PCT Pub. No.: WO2018/051293
PCT Pub. Date: Mar. 22, 2018

(65) Prior Publication Data
US 2019/0209602 A1    Jul. 11, 2019

(30) Foreign Application Priority Data
Sep. 19, 2016 (IT) .................. 102016000093825

(51) Int. Cl.
*A61K 31/7105* (2006.01)
*C12N 15/113* (2010.01)
*A61P 25/00* (2006.01)
*A61P 25/08* (2006.01)
*A61P 25/24* (2006.01)
*A61P 25/28* (2006.01)
*A61P 35/00* (2006.01)
*C12N 15/115* (2010.01)

(52) U.S. Cl.
CPC .......... *A61K 31/7105* (2013.01); *A61P 25/08* (2018.01); *A61P 25/24* (2018.01); *A61P 25/28* (2018.01); *A61P 35/00* (2018.01); *C12N 15/113* (2013.01); *C12N 15/115* (2013.01)

(58) Field of Classification Search
None
See application file for complete search history.

(56) References Cited

U.S. PATENT DOCUMENTS

| 9,078,914 B2 | 7/2015 | Velin et al. | |
| 10,041,073 B2* | 8/2018 | Khvorova | C12N 15/111 |
| 2015/0037299 A1* | 2/2015 | Brodie | A61P 25/16 |
| | | | 424/93.21 |

FOREIGN PATENT DOCUMENTS

WO    2006081284 A2    8/2006

OTHER PUBLICATIONS

International Search Report for International Patent Application No. PCT/IB2017/055617 dated Nov. 29, 2017, 7 pgs.
Laura Stappert et al., "The role of microRNAs in human neural stem cells, neuronal differentiation and subtype specification", Cell and Tissue Research, Aug. 30, 2014 (Aug. 30, 2014), pp. 47-64, vol. 359, Issue 1, Springer Verlag, DE, XP035419580, ISSN: 0302-766X, DOI:10.1007/S00441-014-1981-Y.
Li-Chun Cheng et al., "miR-124 regulates adult neurogenesis in the subventricular zone stem cell niche" Nature Neuroscience, Mar. 15, 2009 (Mar. 15, 2009), pp. 399-408, vol. 12, No. 4, Nature Publishing Group, USA, XP055391621, ISSN: 1097-6256, DOI: 10.1038/nn.2294.
Schouten Marijn et al., "New Neurons in Aging Brains: Molecular Control by Small Non-Coding RNAs", Frontiers in Neuroscience, Jan. 2012 (Jan. 1, 2012), pp. 1-13, vol. 6, Art. 25, XP055389821, DOI: 10.3389/fnins.2012.00025.
Brandon Smith et al., "Large-Scale Expression Analysis Reveals Distinct MicroRNA Profiles at Different Stages of Human Neurodevelopment", PLOS One, Jun. 15, 2010 (Jun. 15, 2010), p. e11109, vol. 5, No. 6, Public Library of Science, USA, XP055389893, DOI: 10.1371j journal.pone.0011109.
Gerhard M. Schratt et al., "A brain-specific microRNA regulates dendritic spine development", Nature, Jan. 19, 2006 (Jan. 19, 2006), pp. 283-289, vol. 439, No. 7074, Nature Publishing Group, XP002617828, ISSN: 0028-0836, DOI: 10.1038/NATURE04367.
Olga Barca-Mayo et al., "Convergent microRNA actions coordinate neocortical development", CMLS Cellular and Molecular Life Sciences, Feb. 12, 2014 (Feb. 12, 2014), pp. 2975-2995, vol. 71, No. 16, Springer Verlag, DE XP055390028, ISSN: 1420-682X, DOI: 10.1007/s00018-014-1576-5.
Meritxell Pons-Espinal et al., "Synergic Functions of miRNAs Determine Neuronal Fate of Adult Neural Stem Cells", Stem Cell Reports, Apr. 1, 2017 (Apr. 1, 2017), pp. 1046-1061, vol. 8, No. 4, ISSCR, USA, XP055390022, ISSN: 2213-6711, DOI: 10.1016fj.stemcr.2017.02.012.
Andersson, T., Rahman, S., Sansom, S.N., Alsiö, J.M., Kaneda, M., Smith, J., O'Carroll, D., Tarakhovsky, A., Livesey, F.J., "Reversible Block of Mouse Neural Stem Cell Differentiation in the Absence of Dicer and MicroRNAs", PloS One, Oct. 18, 2010, vol. 5, Issue, 10, e13453, Public Library of Science, USA.
Babu, H., Claasen, J.-H., Kannan, S., Rünker, A.E., Palmer, T., Kempermann, G., "A protocol for isolation and enriched monolayer cultivation of neural precursor cells from mouse dentate gyrus", Frontiers in Neuroscience, Neurogenesis, Jul. 14, 2011, pp. 1-10, vol. 5, Article 89.

(Continued)

Primary Examiner — Tracy Vivlemore
(74) Attorney, Agent, or Firm — Merchant & Gould P.C.

(57) ABSTRACT

Pharmaceutical compositions are provided which include a microRNA pool capable of promoting, stimulating or increasing neuronal differentiation, as well as methods for treating, ameliorating and/or preventing depression or diseases where damage to nervous tissue occurs, such as neurological diseases, by means of such microRNA pool.

18 Claims, 14 Drawing Sheets
Specification includes a Sequence Listing.

(56) References Cited

OTHER PUBLICATIONS

Beckervordersandforth, R., Tripathi, P., Ninkovic, J., Bayam, E., Lepier, A., Stempfhuber, B., Kirchhoff, F., Hirrlinger, J., Haslinger, A., Lie, D.C., Beckers J., Yoder B., Irmler M., Götz M., "In Vivo Fate Mapping and Expression Analysis Reveals Molecular Hallmarks of Prospectively Isolated Adult Neural Stem Cells", Cell Stem Cell, Resource, Dec. 3, 2010, pp. 744-758, vol. 7, Issue 6, Cell Press, USA.

Beckervordersandforth, R., Deshpande, A., Schäffner, I., Huttner, H.B., Lepier, A., Lie, D.C., Götz, M., "In Vivo Targeting of Adult Neural Stem Cells in the Dentate Gyrus by a Split-Cre Approach", Stem Cell Reports, Feb. 11, 2014, pp. 153-162, vol. 2, ISSCR, USA.

Bonaguidi, M.A., Song, J., Ming, G., Song, H., "A unifying hypothesis on mammalian neural stem cell properties in the adult hippocampus", Current Opinion in Neurobioly, Oct. 2012, pp. 754-761, vol. 22, Issue 5, Elsevier.

Braun, S.M.G., Machado, R.A.C., Jessberger, S., "Temporal Control of Retroviral Transgene Expression in Newborn Cells in the Adult Brain", Stem Cell Reports, Aug. 6, 2013, pp. 114-122, vol. 1, ISSCR, USA.

Cahoy, J.D., Emery, B., Kaushal, A., Foo, L.C., Zamanian, J.L., Christopherson, K.S., Xing, Y., Lubischer, J.L., Krieg, P.A., Krupenko, S.A., Thompson W.J., Barres A., "A Transcriptome Database for Astrocytes, Neurons, and Oligodendrocytes: A New Resource for Understanding Brain Development and Function", The Journal of Neuroscience, Jan. 2, 2008, pp. 264-278, vol. 28, Issue 1, JNeuroshi, Society for Neuroscience, USA.

Dibajnia, P., Morshead, C.M., "Role of neural precursor cells in promoting repair following stroke", Acta Pharmacologica Sinica, Jan. 2013, pp. 78-90, vol. 34, No. 1, Chinese Pharmacological Society, Shanghai Institute of Materia Medica, Nature Publishing Group.

Doetsch, F., Petreanu, L., Caille, I., Garcia-Verdugo, J.M., Alvarez-Buylla, A., "EGF Converts Transit-Amplifying Neurogenic Precursors in the Adult Brain into Multipotent Stem Cells", Neuron, Dec. 19, 2002, pp. 1021-1034, vol. 36, Cell Press, USA.

Encinas, J.M., Vaahtokari, A., Enikolopov, G., "Fluoxetine targets early progeni-tor cells in the adult brain", PNAS, May 23, 2006, pp. 8233-8238, vol. 103, No. 21, National Academy of Sciences, USA.

Encinas, J.M., Michurina, T.V., Peunova, N., Park, J.-H., Tordo, J., Peterson, D.A., Fishell, G., Koulakov, A., Enikolopov, G., "Division-Coupled Astrocytic Differentiation and Age-Related Depletion of Neural Stem Cells in the Adult Hippocampus", Cell Stem Cell, May 6, 2011, pp. 566-579, vol. 8, Issue 5, Cell Press, USA.

Gage, F.H., Temple, S., "Neural Stem Cells: Generating and Regenerating the Brain", Neuron, Oct. 30, 2013, pp. 588-601, vol. 80, Issue 3, Cell Press, Elsevier Inc.

Gargaro, A.C., Sakamoto, A.C., Bianchin, M.M., Geraldi, C. De V.L., Scorsi-Rosset, S., Coimbra, E. R., Carlotti, C.G. Jr, Assirati, J.A., Velasco, T.R., "Atypical neuropsy-chological profiles and cognitive outcome in mesial temporal lobe epilepsy", Epilepsy & Behavior, Jun. 2013, pp. 461-469, vol. 27, Issue 3, Elsevier Inc.

Gibbons, M.B., Smeal, R.M., Takahashi, D.K., Vargas, J.R., Wilcox, K.S., "Contributions of Astrocytes to Epileptogenesis Following Status Epilepticus: Opportunities for Preventive Therapy?", Neurochemistry International, Dec. 2013, pp. 660-669, vol. 63, Issue 7, Elsevier Ltd.

Gleeson, J.G., Lin, P.T., Flanagan, L.A., Walsh, C.A., "Doublecortin is a Micro-Tubule-Associated Protein and Is Expressed Widely by Migrating Neurons", Neuron, Jun. 1999, pp. 257-271, vol. 23, Issue 2, Cell Press, USA.

Heuser, K., Taubøll, E., Nagelhus, E.A., Cvancarova, M., Petter Ottersen, O., Gjer-Stad, L., "Phenotypic characteristics of temporal lobe epilepsy: the impact of hippo-campal sclerosis", Acta Neurologica Scandinavica, Aug. 2009, pp. 8-13, vol. 120, Issue s189, John Wiley & Sons A/S.

Kempermann, G.,"The Pessimist's and Optimist's views of Adult Neurogenesis", Cell, Jun. 24, 2011, pp. 1009-1011, vol. 145, Issue 7, Cell Press, Elsevier Inc.

Leker, R.R., Lasri, V., Chernoguz, D., "Growth factors improve neurogenesis and outcome after focal cerebral ischemia, Journal of Neural Transmission", Nov. 2009, pp. 1397-1402, vol. 116, Issue 11, Springer Verlag, Vienna, Austria.

Madisen, L., Zwingman, T.A., Sunkin, S.M., Seung Wook Oh, Zariwala, H.A., Gu, H., Ng, L.L., Palmiter, R.D., Hawrylycz, M.J., Jones, A.R., Lein, E.S., Zeng H., "A robust and high-throughput Cre reporting and characterization system for the whole mouse brain", Nature Neuroscience, Jan. 2010, pp. 133-140, vol. 13, Issue 1, Springer Nature Publishing Group.

Malberg, J.E., Eisch, A.J., Nestler, E.J., Duman, R.S., "Chronic Antidepressant Treatment Increases Neurogenesis in Adult Rat Hippocampus", The Journal of Neuroscience, Dec. 15, 2000, pp. 9104-9110, vol. 20, Issue 24, JNeurosci, Society for Neuroscience, USA.

Marlatt, M.W., Lucassen, P.J., "Neurogenesis and Alzheimer's disease: biology and pathophysiology in mice and men", Current Alzheimer Research, 2010, pp. 113-125, vol. 7, Issue 2, Bentham Science Publishers Ltd.

Mullen, R.J., Buck, C.R., Smith, A.M., "NeuN, a neuronal specific nuclear protein in vertebrates, Development", Sep. 1, 1992, pp. 201-211, vol. 116, Issue 1, The Company of Biologists Limited, Cambridge, UK.

Murchison, E.P., Partridge, J.F., Tam, O.H., Cheloufi, S., Hannon, G.J., "Characterization of Dicer-deficient murine embryonic stem cells", PNAS, Aug. 23, 2005, pp. 12135-12140, vol. 102, No. 34, National Academy of Sciences, USA.

Pons-Espinal, M., De Lagran, M.M., Dierssen, M., "Functional implications of hippocampal adult neurogenesis in intellectual disabilities", Amino Acids, Jul. 2013, vol. 45, Issue 1, Springer Verlag, Vienna, Austria.

Santarelli, L., Saxe, M., Gross, C., Surget, A., Battaglia, F., Dulawa, S., Weisstaub, N., Lee, J., Duman, R., Arancio, O., Belzung C., Hen R., "Requirement of Hippocampal Neurogenesis for the Behavioral Effects of Antidepressants", Science, Aug. 8, 2003, pp. 805-809, vol. 301, American Association for the Advancement of Science (AAAS), Washington D.C., USA.

Shimada, I.S., Lecomte, M.D., Granger, J.C., Quinlan, N.J., Spees, J.L., "Self-renewal and differentiation of reactive astrocyte-derived neural stem/progenitor cells isolated from the cortical peri-infarct area after stroke", Journal of Neuroscience, Jun. 6, 2012, pp. 7926-7940, vol. 32, Issue 23, JNeurosci, Society for Neuroscience, USA.

Sierra, A., Martín-Suárez, S., Valcárcel-Martín, R., Pascual-Brazo, J., Aelvoet, S.-A., Abiega, O., Deudero, J.J., Brewster, A.L., Bernales, I., Anderson, A.E., Baekelandt, V., Maletić-Savatić, M., Encinas, J.M., "Neuronal Hyperactivity Accelerates Depletion of Neural Stem Cells and Impairs Hippocampal Neurogenesis", Cell Stem Cell, May 7, 2015, pp. 488-503 vol. 16, Issue 5, Cell Press, USA.

Walker, T.L., Kempermann, G., "One Mouse, Two Cultures: Isolation and Culture of Adult Neural Stem Cells from the Two Neurogenic Zones of Individual Mice", Journal of Visualized Experiments, Feb. 2014, pp. 1-9, vol. 84, JoVE e51225, doi:10.3791/51225, Creative Commons Attribution—NonCommercial—NoDerivatives 3.0 Unported License.

Wang, F., Hao, H., Zhao, S., Zhang, Y., Liu, Q., Liu, H., Liu, S., Yuan, Q., Bing, L., Ling, E.-A., Hao, A., "Roles of activated astrocyte in neural stem cell proliferation and differentiation", Stem Cell Research, Jul. 2011, pp. 41-53, vol. 7, Issue 1, Elsevier B.V.

* cited by examiner

SEQUENCE LISTING

<160> NUMBER OF SEQ ID NOS: 22

<210> SEQ ID NO 1
<211> LENGTH: 20
<212> TYPE: RNA

```
<213> ORGANISM: Homo sapiens

<400> SEQUENCE: 1
uaaggcacgc ggugaaugcc                                          20

<210> SEQ ID NO 2
<211> LENGTH: 22
<212> TYPE: RNA
<213> ORGANISM: Homo sapiens

<400> SEQUENCE: 2
ucggauccgu cugagcuugg cu                                       22

<210> SEQ ID NO 3
<211> LENGTH: 22
<212> TYPE: RNA
<213> ORGANISM: Homo sapiens

<400> SEQUENCE: 3
ugugacuggu ugaccagagg gg                                       22

<210> SEQ ID NO 4
<211> LENGTH: 23
<212> TYPE: RNA
<213> ORGANISM: Homo sapiens

<400> SEQUENCE: 4
uauggcuuuu uauuccuaug uga                                      23

<210> SEQ ID NO 5
<211> LENGTH: 23
<212> TYPE: RNA
<213> ORGANISM: Homo sapiens

<400> SEQUENCE: 5
ucuacagugc acgugucucc agu                                      23

<210> SEQ ID NO 6
<211> LENGTH: 21
<212> TYPE: RNA
<213> ORGANISM: Homo sapiens

<400> SEQUENCE: 6
uugugcuuga ucuaaccaug u                                        21

<210> SEQ ID NO 7
<211> LENGTH: 22
<212> TYPE: RNA
<213> ORGANISM: Homo sapiens

<400> SEQUENCE: 7
gccugcuggg guggaaccug gu                                       22

<210> SEQ ID NO 8
<211> LENGTH: 22
<212> TYPE: RNA
<213> ORGANISM: Homo sapiens

<400> SEQUENCE: 8
aucauagagg aaaauccaug uu                                       22

<210> SEQ ID NO 9
<211> LENGTH: 22
```

```
<212> TYPE: RNA
<213> ORGANISM: Homo sapiens

<400> SEQUENCE: 9
gaaguuguuc gugguggauu cg                                              22

<210> SEQ ID NO 10
<211> LENGTH: 21
<212> TYPE: RNA
<213> ORGANISM: Homo sapiens

<400> SEQUENCE: 10
uaguagaccg uauagcguac g                                               21

<210> SEQ ID NO 11
<211> LENGTH: 23
<212> TYPE: RNA
<213> ORGANISM: Homo sapiens

<400> SEQUENCE: 11
aaggagcuua caaucuagcu ggg                                             23

<210> SEQ ID NO 12
<211> LENGTH: 20
<212> TYPE: RNA
<213> ORGANISM: Mus musculus

<400> SEQUENCE: 12
uaaggcacgc ggugaaugcc                                                 20

<210> SEQ ID NO 13
<211> LENGTH: 22
<212> TYPE: RNA
<213> ORGANISM: Mus musculus

<400> SEQUENCE: 13
ucggauccgu cugagcuugg cu                                              22

<210> SEQ ID NO 14
<211> LENGTH: 22
<212> TYPE: RNA
<213> ORGANISM: Mus musculus

<400> SEQUENCE: 14
ugugacuggu ugaccagagg gg                                              22

<210> SEQ ID NO 15
<211> LENGTH: 23
<212> TYPE: RNA
<213> ORGANISM: Mus musculus

<400> SEQUENCE: 15
uauggcuuuu uauuccuaug uga                                             23

<210> SEQ ID NO 16
<211> LENGTH: 22
<212> TYPE: RNA
<213> ORGANISM: Mus musculus

<400> SEQUENCE: 16
ucuacagugc acgugucucc ag                                              22

<210> SEQ ID NO 17
```

-continued

```
<211> LENGTH: 21
<212> TYPE: RNA
<213> ORGANISM: Mus musculus

<400> SEQUENCE: 17
uugugcuuga ucuaaccaug u                                         21

<210> SEQ ID NO 18
<211> LENGTH: 22
<212> TYPE: RNA
<213> ORGANISM: Mus musculus

<400> SEQUENCE: 18
gccugcuggg guggaaccug gu                                        22

<210> SEQ ID NO 19
<211> LENGTH: 21
<212> TYPE: RNA
<213> ORGANISM: Mus musculus

<400> SEQUENCE: 19
aucauagagg aacauccacu u                                         21

<210> SEQ ID NO 20
<211> LENGTH: 22
<212> TYPE: RNA
<213> ORGANISM: Mus musculus

<400> SEQUENCE: 20
gaaguuguuc gugguggauu cg                                        22

<210> SEQ ID NO 21
<211> LENGTH: 21
<212> TYPE: RNA
<213> ORGANISM: Mus musculus

<400> SEQUENCE: 21
uaguagaccg uauagcguac g                                         21

<210> SEQ ID NO 22
<211> LENGTH: 23
<212> TYPE: RNA
<213> ORGANISM: Mus musculus

<400> SEQUENCE: 22
aaggagcuua caaucuagcu ggg                                       23
```

MIRNA PHARMACEUTICAL COMPOSITIONS AND THERAPEUTIC USES THEREOF

CROSS-REFERENCE TO RELATED APPLICATIONS

This application is a National Phase Application of PCT International Application No. PCT/IB2017/055617, International Filing Date, Sep. 18, 2017, claiming priority to Italian Patent Application No. 102016000093825, filed Sep. 19, 2016 each of which is hereby incorporated by reference in its entirety.

FIELD OF THE INVENTION

The present invention relates to a pharmaceutical composition which is suitable to promote neuronal differentiation and therefore useful in the treatment and prevention of age-related neurodegeneration, as well as diseases where damage to the nervous tissue occurs, such as neurodegenerative diseases, cancer, stroke, epilepsy.

BACKGROUND OF THE INVENTION

Ageing is the main risk factor for neurodegeneration and cognitive decline associated therewith. As life expectancy is increasing, these phenomena will become of great social and economic importance. By 2050 the number of people over 60 years of age will be doubled, reaching 2 billion people, corresponding to approximately 22% of the world's population (Bulletin of the World Health Organization, 2014). In 2050, approximately 50% of adults over the age of 85 will suffer from cognitive decline caused by neurodegeneration. Among these, about 20 million people will reside in Europe, which will lead to a huge increase in European health system expenditure. It is therefore necessary to deepen the understanding of the differences between an old and a young brain, and how environmental factors can affect age-related decline in brain function.

Neuronal stem cells residing in the two main neurogenic niches of the adult mammalian brain (the subventricular zone—SVZ—of the lateral ventricle, and the subgranular zone of the hippocampal dentate gyrus—DG—) are highly heterogeneous populations of radial glia-like precursor cells, which have astrocytic properties, express bona fide stem cell markers and rarely divide. These cells have the ability to self-renew and differentiate both into neurons and glial cells. The mechanism underlying the fate of adult hippocampal neuronal stem cells (aNSC) is a very debated topic (Bonaguidi et al., 2012; Kempermann, 2011).

It is believed that age-related loss of adult neurogenesis is one of the causes of many neurodegenerative diseases and age-related cognitive decline. On the other hand, a healthy lifestyle can have a positive effect on brain health, "rejuvenating" adult neuronal cells at various levels. Accordingly, a controlled increase in brain plasticity could be a promising path to the development of future regenerative therapies.

Modern society is also affected by a variety of neurodegeneration-related human diseases, such as Alzheimer's disease, Parkinson's disease, stroke, trauma, and so on. Neuronal stem cell transplant strategies for the treatment of various central nervous system disorders provide a new direction with good prospects. An alternative strategy would be to promote neuronal regeneration from resident stem cells, during ageing or after trauma.

In all cases, the understanding and control of the molecular mechanisms underlying adult neurogenesis would open up new possibilities for preventing and treating age- or neurodegeneration-related loss of neurogenesis, pathological formation of undesirable cells, such as glial cells activated by trauma/epilepsy, as well as new possibilities for developing adult neuronal stem cell transplant therapies.

Although regenerative and neuronal stem cell transplantation therapies have enormous potential, there are still many problems to be solved before they can be actually applied in the clinic. For example, fate determination of transplanted neuronal stem cells must be controlled to avoid that only a small fraction thereof differentiates into neurons and that most, instead, differentiate into astrocytes. It is important to know that astrocytes not only do not contribute to the repair of neural circuits damaged after trauma, but that these cells participate in the formation of glial scars that may be a hindrance to healing. Another example is provided by studies that show that trauma or epilepsy can damage adult neurogenesis. In fact, during epilepsy, adult neuronal stem cells can directly generate reactive astrocytes (Sierra et al., 2015). It has been suggested that neurogenic impairment, in turn, contributes to cognitive deficits (Gargaro et al., 2013) and psychiatric comorbidities (Heuser et al., 2009) associated with medial temporal lobe epilepsy (MTLE), a chronic condition in which one-third of patients fail to respond to medical treatment. In parallel, reactive astrocytes and neuronal abnormalities have been proposed as mechanisms that cause both pathology and endogenous repair in epileptogenesis (Gibbons et al., 2013), but the mechanism by which adult neuronal stem cells could participate in these processes is not yet fully known.

As of today, most of the transplant/regeneration paradigms have not allowed increased neurogenesis and, on the contrary, have favoured astrocyte differentiation (Dibajnia and Morshead, 2013; Shimada et al., 2012). In addition, treatment with growth factors, used to increase the differentiation of new neurons from neuronal stem cells and their survival (Leker et al., 2009), were correlated with glioma formation (Doetsch et al., 2002).

Therefore, new strategies are urgently required for increasing the neurogenic capacity of neuronal stem cells, while hampering their differentiation into astrocytes and preventing their premature exhaustion.

SUMMARY OF THE INVENTION

To meet these and other needs, the present invention provides pharmaceutical compositions, methods and treatment kits as defined and claimed herein.

The invention is further described in the examples below, with reference to the attached drawings.

DETAILED DESCRIPTION

Figure 1:
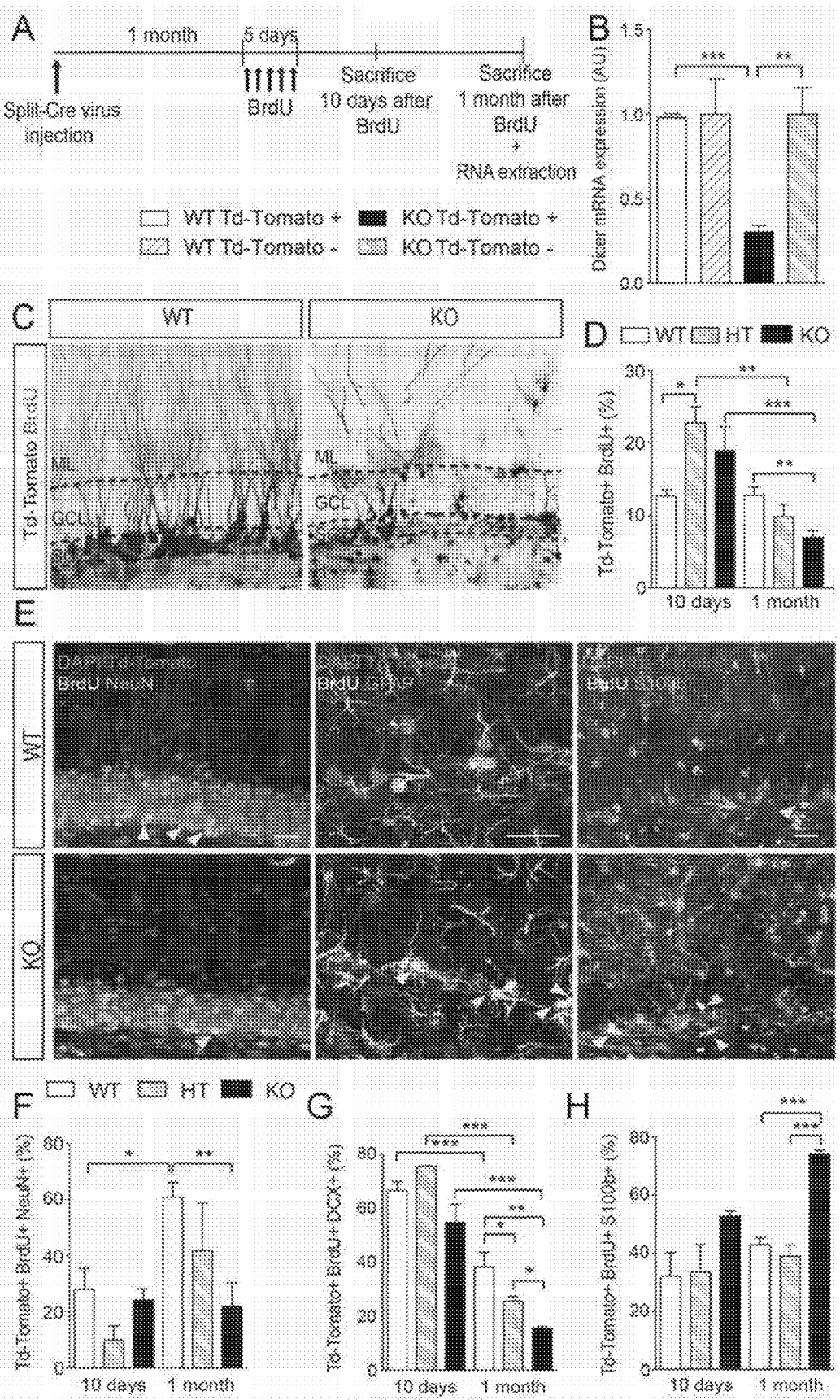
FIG. 1 shows that Split Cre virus-mediated Dicer ablation in vivo prevents neuronal differentiation and survival, but not astrogliogenesis. A: Schematic representation of the procedure used for ablating Dicer in vivo using a Split-Cre lentiviral approach to assess aNSC survival and differentiation. B: qPCR relative quantification of Dicer mRNA from FACS-sorted Td-Tomato+ aNSCs obtained two months after Split-Cre virus injection. C and E: Representative micrographs showing Td-Tomato+ recombinant cells from $Dicer^{wt/wt}$ $Td\text{-}Tomato^{flox/wt}$ (WT) and $Dicer^{flox/flox}$ $Td\text{-}Tomato^{flox/wt}$ (KO) mice 1 month after BrdU injections, which express BrdU (C), co-express BrdU and NeuN (E, left panel), co-express BrdU and GFAP (E, middle panel), and co-express BrdU and S100b (E, right panel). D: Percentage of Td-Tomato+ cells expressing BrdU 10 days or 1 month after BrdU injections. F, G and H: Percentage of Td-Tomato+ BrdU+ cells co-expressing NeuN (F), DCX (G) or S100b (H) 10 days or 1 month after BrdU injections. ML: Molecular layer. GCL: Granular cell layer. SGZ: Subgranular zone. Data are expressed as mean+/−SEM. N=4-6 mice per group. Scale bars=20 μm. An unpaired t-test was used for Dicer mRNA expression analysis. A one-way ANOVA Bonferroni post-hoc test was used to analyse cell marker quantification. *$p<0.05$; $p<0.01$; *$p<0.001$.

In the present specification, the terms "microRNA" or "miRNA" refer to short endogenous non-encoded single-stranded RNA molecules with a length generally ranging from 20 to 25 nucleotides.

The present invention is based on the results obtained by the inventors in the experimentation and research activities described in the following experimental section. In short, adult neurogenesis is known to require a precise control of neuronal stem cell fate determination, where neurogenesis is favoured at the expense of astrocyte generation. Experimental evidence shows that microRNAs (miRNAs) are involved in this process during development, but their role in hippocampal stem cells (aNSCs) has so far been unclear. To study these mechanisms, the inventors have chosen to focus their attention on Dicer, an endonuclease enzyme essential for miRNA biogenesis and other processes involving RNA interference. By specific in vivo and in vitro ablation of Dicer in aNSCs, the inventors have demonstrated that miRNAs are crucial for the generation of new neurons, but not astrocytes, in the adult murine hippocampus. Moreover, by re-administration of a pool of eleven miRNAs (SEQ ID NO: 1-11), the neurogenesis previously damaged by Dicer ablation could be rescued, while administration of individual miRNAs or subgroups of the set of eleven miRNAs forming the object of the invention had no effect.

Thus, the inventors have identified a new pool of miRNAs that acts synergistically in adult neuronal stem cell fate determination, favouring neurogenesis at the expense of astrogliogenesis. This opens the way to a new pharmacological strategy to increase the efficiency of neurogenesis induction in vivo and in vitro.

The present invention can be applied to prevent or treat age-related loss of neurogenesis (Encinas et al., 2011; Marlatt and Lucassen, 2010; Pons-Espinal et al., 2013), as well as diseases where damage to the nervous tissue occurs, such as tumours (e.g. glioblastoma), and/or the formation of glial cells activated, for example, after trauma, stroke, epilepsy or transplant (Dibajnia and Morshead, 2013; Doetsch et al., 2002; Shimada et al., 2012; Sierra et al., 2015).

Although the experimental studies have been carried out in mouse cells with murine miRNAs, the results obtained are directly applicable to humans since the miRNA sequences are conserved between humans and mice. Table 1 below shows that the mouse and human miRNA sequences are identical, except for miR-139-5p MIMAT0000656 (SEQ ID NO: 16 and 5) and miR-376b-3p MIMAT0001092 (SEQ ID NO: 19 and 8), in which there is a single base difference at the 3' terminus. Table 1 also shows the seed sequence of each miRNA (underlined), i.e. the sequence of the miRNA active region that determines target recognition and is usually composed of 6-8 nucleotides, and typically comprises the region between nucleotide 2 and nucleotide 10 from the miRNA's 5'-end. Since the seed sequence is the active portion of the miRNA, miRNAs with the same seed sequence are predicted to have similar activities.

TABLE 1

| | | | |
|---|---|---|---|
| mmu-miR-124-3p | MIMAT0000134 | (SEQ ID NO: 12) | 5' U<u>AAGGCAC</u>GCGGUGAAUGCC |
| hsa-miR-124-3p | MIMAT0000422 | (SEQ ID NO: 1) | 5' U<u>AAGGCAC</u>GCGGUGAAUGCC |

TABLE 1-continued

```
mmu-miR-127-3p   MIMAT0000139 (SEQ ID NO: 13) 5' UCGGAUCCGUCUGAGCUUGGCU hsa-miR-127-3p   MIMAT0000446 (SEQ ID NO:  2) 5' UCGGAUCCGUCUGAGCUUGGCU mmu-miR-134-5p   MIMAT0000146 (SEQ ID NO: 14) 5' UGUGACUGGUUGACCAGAGGGG hsa-miR-134-5p   MIMAT0000447 (SEQ ID NO:  3) 5' UGUGACUGGUUGACCAGAGGGG mmu-miR-135a-5p  MIMAT0000147 (SEQ ID NO: 15) 5' UAUGGCUUUUUAUUCCUAUGUGA hsa-miR-135a-5p  MIMAT0000428 (SEQ ID NO:  4) 5' UAUGGCUUUUUAUUCCUAUGUGA mmu-miR-139-5p   MIMAT0000656 (SEQ ID NO: 16) 5' UCUACAGUGCACGUGUCUCCAGhsa-miR-139-5p   MIMAT0000250 (SEQ ID NO:  5) 5' UCUACAGUGCACGUGUCUCCAGU mmu-miR-218-5p   MIMAT0000663 (SEQ ID NO: 17) 5' UUGUGCUUGAUCUAACCAUGU hsa-miR-218-5p   MIMAT0000275 (SEQ ID NO:  6) 5' UUGUGCUUGAUCUAACCAUGU mmu-miR-370-3p   MIMAT0001095 (SEQ ID NO: 18) 5' GCCUGCUGGGGUGGAACCUGGU hsa-miR-370-3p   MIMAT0000722 (SEQ ID NO:  7) 5' GCCUGCUGGGGUGGAACCUGGU mmu-miR-376b-3p  MIMAT0001092 (SEQ ID NO: 19) 5' AUCAUAGAGGAACAUCCACUUhsa-miR-376b-3p  MIMAT0002172 (SEQ ID NO:  8) 5' AUCAUAGAGGAAAAUCCAUGUU mmu-miR-382-5p   MIMAT0000747 (SEQ ID NO: 20) 5' GAAGUUGUUCGUGGUGGAUUCG hsa-miR-382-5p   MIMAT0000737 (SEQ ID NO:  9) 5' GAAGUUGUUCGUGGUGGAUUCG mmu-miR-411-5p   MIMAT0004747 (SEQ ID NO: 21) 5' UAGUAGACCGUAUAGCGUACG hsa-miR-411-5p   MIMAT0003329 (SEQ ID NO: 10) 5' UAGUAGACCGUAUAGCGUACG mmu-miR-708-5p   MIMAT0004828 (SEQ ID NO: 22) 5' AAGGAGCUUACAAUCUAGCUGGG hsa-miR-708-5p   MIMAT0004926 (SEQ ID NO: 11) 5' AAGGAGCUUACAAUCUAGCUGGG
```

In light of the above, a first aspect of the invention is a pharmaceutical composition comprising a plurality of microRNAs and a pharmaceutically acceptable carrier and/or diluent and/or excipient, said plurality of micro mRNAs comprising a microRNA comprising nucleotides 1-8 of SEQ ID NO:1, a microRNA comprising nucleotides 2-11 of SEQ ID NO:2, a microRNA comprising nucleotides 2-11 of SEQ ID NO:3, a microRNA comprising nucleotides 2-8 of SEQ ID NO:4, a microRNA comprising nucleotides 2-11 of SEQ ID NO:5, a microRNA comprising nucleotides 2-8 of SEQ ID NO:6, a microRNA comprising nucleotides 2-11 of SEQ ID NO:7, a microRNA comprising nucleotides 2-11 of SEQ ID NO:8, a microRNA comprising nucleotides 2-11 of SEQ ID NO:9, a microRNA comprising nucleotides 2-11 of SEQ ID NO:10 and a microRNA comprising nucleotides 2-11 of SEQ ID NO:11, wherein the nucleotide positions are indicated with reference to the 5' terminus of the sequence.

A preferred embodiment of the invention is a pharmaceutical composition comprising a pharmaceutically acceptable carrier and/or diluent and/or excipient, and the following pool of microRNAs:
hsa-miR-124-3p MIMAT0000422 (SEQ ID NO:1);
hsa-miR-127-3p MIMAT0000446 (SEQ ID NO:2);
hsa-miR-134-5p MIMAT0000447 (SEQ ID NO:3);
hsa-miR-135a-5p MIMAT0000428 (SEQ ID NO:4);
hsa-miR-139-5p MIMAT0000250 (SEQ ID NO:5);
hsa-miR-218-5p MIMAT0000275 (SEQ ID NO:6);
hsa-miR-370-3p MIMAT0000722 (SEQ ID NO:7);
hsa-miR-376b-3p MIMAT0002172 (SEQ ID NO:8);
hsa-miR-382-5p MIMAT0000737 (SEQ ID NO:9);
hsa-miR-411-5p MIMAT0003329 (SEQ ID NO:10); and
hsa-miR-708-5p MIMAT0004926 (SEQ ID NO:11).

The pharmaceutical composition of the invention is suitable for use as a medicament, in particular as a medicament capable of promoting, stimulating or increasing neuronal differentiation, preferably in the human being.

The term "neuronal differentiation" refers, in particular, to the differentiation of adult neuronal stem cells into neurons.

Thanks to its action on neuronal differentiation, the pharmaceutical composition of the invention is suitable for use in the therapeutic treatment or prevention of a neurodegenerative disease, an age-related neurodegenerative condition, neurodegeneration-related cognitive decline, a tumour disease of the nervous tissue, such as in particular glioblastoma, and damage to the nervous tissue caused by epilepsy and/or stroke. It is also suitable for use as an antidepressant medicament. In fact, antidepressants, such as selective serotonin reuptake inhibitors (SSRIs), like fluoxetine paroxetine (Prozac) are known to stimulate adult neurogenesis (Encinas et al., 2006). It is also known that in the absence of adult neurogenesis, antidepressants have no effect (Malberg et al., 2000; Santarelli et al., 2003). Since the composition of the present invention stimulates adult hippocampal neurogenesis, it is expected to have beneficial effects on such behaviours as those resulting from depression, by means of its action on neurogenesis stimulation.

A second aspect of the invention is a kit comprising a plurality of microRNAs as defined above with reference to the composition, and a pharmaceutically acceptable carrier and/or diluent and/or excipient, as a combined preparation

EXAMPLES

Example 1

Experimental Procedures
Animals

The mice were housed under standard laboratory conditions at the animal facility of the Istituto Italiano di Tecnologia (IIT), Genoa, Italy. All experiments and procedures were approved by the Italian Ministry of Health (Permits No. 056/2013 and 214/2015-PR) and local Animal Use Committee, and were carried out in accordance with the European legislation for use and care of laboratory animals. Dicerflox/flox mice (Murchison et al., 2005) were crossed with Td-Tomato flox/wt knock-in reporter mice (Jackson lab stock number 007908; (Madisen et al., 2010). Dicer wt/wt Td-Tomato flox/wt (Dicer WT); Dicer flox/wt Td-Tomato flox/wt (Dicer HT) and Dicer flox/flox Td-Tomato flox/wt (Dicer cKO) mice were used for all experiments. All animals were 8 weeks old at the time of infection with the virus expressing Split-Cre-Recombinase (Beckervordersandforth et al., 2010). One month later, the mice received a daily intraperitoneal injection of BrdU (50 mg/kg) for 5 days. The animals were sacrificed and analysed 10 days or 1 month after BrdU injections.

aNSC Preparation, Culture Conditions and miRNA Administration

Adult neural stem cells (aNSCs) were obtained from hippocampi of Dicer wt/wt Td-Tomato flox/wt (Dicer WT), Dicer flox/wt Td-Tomato flox/wt (Dicer HT) and Dicer flox/flox Td-Tomato flox/wt (Dicer cKO) mice 6 to 8 weeks old and expanded in proliferation medium as described (Babu et al., 2011; Walker and Kempermann, 2014). The Dicer gene was removed from proliferating aNSCs by nucleofection (Amaxa, Lonza) of 5 µg of Cre-recombinase-expressing vector under the control of the constitutive chicken β-actin promoter (CAG) fused with the CMV promoter enhancer (pCAGGS-CRE). Two hours before fixing, BrdU (Sigma-Aldrich) was added to the aNSCs in proliferation medium at a final concentration of 10 µM. Differentiation: aNSCs were plated at 1,2*10E4 cells/cm$^2$ in culture medium supplemented with FGF (20 ng/ml) for 24 hours. The medium was then exchanged with medium containing B27 with retinoic acid and FGF (5 ng/ml) for 24 hours, and FGF (1 ng/ml) over the following 4 days. Cells were differentiated in culture for 6 days in vitro (DIV). Astrocyte differentiation medium: aNSCs were plated at a density of 1.2*10E4 cells/cm$^2$ in growth medium with 10% FBS without growth factors for 6 DIV. Retrovirus-mediated inducible neuronal differentiation: a viral construct expressing Ascl1-ERT2 and infection conditions were as previously described (Braun et al., 2013). Neuronal differentiation was induced by removal of growth factors and addition of 0.5 mM OH-TAM (Sigma) for 2 days. The medium was changed every two-three days. Cells were fixed at 7, 14 or 21 days after exposure to OH-TAM. miRNA administration: proliferating aNSCs were nucleofected (Amaxa, Lonza) with 250 nM "control mimics" (Negative control, CN-001000-01-05; Dharmacon), or with a mix of individual "miRNA Mimics" (Dharmacon), each at 25 nM plus Negative control up to a final concentration of 250 nM. When the "miRNA mimics" were transfected as a pool, an equimolar concentration was used, up to a final concentration of 250 nM. 24 hours after nucleofection, the cells were plated in differentiation medium and 6 days later were harvested for analysis.

Immunofluorescence and Western Blot

Immunofluorescence staining on brain slices was carried out in one out of six sections covering the entire dorsal hippocampus. Primary antibodies: rat anti-BrdU (1:200; ab-6326; Abcam), rabbit anti-doublecortin (1:1000; ab18723: Abcam), rabbit GFAP (1:1000; Z-0334; Dako), mouse anti-S100b (1:250; Sigma), mouse anti-NeuN (1:250; Millipore). Secondary fluorescent antibodies (1/1000; Goat Alexa 488, 568, and 647 nm, Invitrogen). Images were obtained with the confocal A1 Nikon Inverted microscope SFC with a 40× objective. Quantification and analysis in the DG (dentate gyrus) was performed using the NIS-Elements software (Nikon). Immunofluorescence on cell cultures was performed as previously described (Babu et al., 2011). Primary antibodies: rat anti-BrdU (1:200; ab-6326; Abcam), goat anti-doublecortin (1:200; Santacruz), rabbit anti-doublecortin (1:500; ab18723; Abcam), rabbit GFAP (1:1000; Z-0334; Dako), Abcam), rat anti-Nestin (1:200; BD-Pharmigen), rat anti-pH3 (1:500; Abcam), rabbit anti-Sox2 (1:500; Millipore), mouse anti-S100b (1:500; Sigma). Alexa Fluor 488-conjugated secondary antibodies (Invitrogen) were used at 1:1000 (obtained in goat); or 1:500 (donkey anti-goat). Images were obtained using the Nikon Eclipse microscope at 20× or 40× magnifications. Cell Counter Plugin in the Image J software (Macbiophotonics) was used to keep track of the counted cells.

Western blot: Proteins were extracted from aNSCs either under proliferation or differentiation conditions at the indicated time points with RIPA buffer containing protease inhibitors (Complete mini EDTA-free, Roche), separated by SDS-PAGE on a 10% Tris gradient gel, and transferred to a nitrocellulose membrane (Bio-Rad). The membranes were probed overnight using the following primary antibodies: rabbit GFAP (1:5000; Z-0334; Dako) and rat anti-Nestin (1:1000; BD-Pharmigen) and HRP-conjugated secondary antibodies (1:2500 Promega). For loading controls, membranes were stripped and re-probed with antiglyceraldehyde 3-phosphate dehydrogenase antibody (GAPDH; Applied Biosystems AM4300). Bands were detected by ECL (Millipore) using ImageQuant LAS 4000 mini (GE Healthcare) and quantified using the ImageJ software.

RNA Extraction and Quantitative PCR

RNA extraction and cDNA preparation: Sixty-eight mice (each Dicer genotype) were sacrificed at the indicated time points. The DG aNSCs were dissociated with the Neural Tissue Dissociation Kit P (Miltenyi Biotec), and FACS-sorted cells were immediately processed for RNA extraction. Cre-nucleofected aNSCs in proliferative medium, or differentiated, were harvested at the indicated time points. Total RNA was extracted with the QIAzol protocol (Qiagen), and RNA was purified with the RNeasy Mini kit or the miRNeasy Mini Kit (Qiagen) following the manufacturer's instructions. cDNA synthesis (from mRNA) was obtained by the ImProm-II™ reverse transcriptase (Promega); cDNA (from miRNA) was prepared with the miScript II RT kit using the HiSpec buffer (Qiagen) according to the manufacturer's instructions. mRNA was quantified with the QuantiFast SYBR Green PCR Kit (Qiagen) on the ABI-7500 Real-Time PCR system (Applied Biosystems). Each sample was normalized to GAPDH or actin levels. miRNAs were quantified with the Mouse Cell Differentiation & Development miScript miRNA PCR Array (Qiagen) and miScript SYBR Green PCR kit (Qiagen) following the manufacturer's recommendations on the ABI-7500 Real-Time PCR system (Applied Biosystems) or with TaqMan® Array Rodent MicroRNA A Cards Set v3.0 (Thermo Fisher) following the manufacturer's recommendations with a ViiA 7 Real-Time PCR system (Thermo Fisher).

Statistical Analysis

Data are presented as mean+/−standard error of the mean and were analysed with Prism 6 (GraphPad, San Jose, Calif., USA). Statistical significance was assessed with a two-tailed unpaired t-test for two experimental groups. For experiments with three or more groups, a one-way ANOVA with Bonferroni's post-hoc multiple comparison test was used. Results were considered significant when $P<0.05$.

Results

Split Cre Virus-Mediated Dicer Ablation In Vivo Impairs Neurogenesis, Neuronal Maturation and Survival, but not Astrogliogenesis, in the Adult Hippocampus To study the role of Dicer in adult hippocampal neurogenesis in vivo, the inventors crossed a murine line carrying a conditional allele for Dicer (Dicerflox, (Murchison et al., 2005), with a Cre-inducible reporter murine line (Td-Tomatoflox, (Madisen et al., 2010). To obtain conditional ablation of Dicer in bona fide Type 1 aNSCs, Split-Cre viruses (FIG. 1A) were injected in the DG of 8 weeks-old Dicer wt/wt Td-Tomato flox/wt (WT), Dicer flox/wt Td-Tomato flox/wt Dicer (HT), and Dicer flox/flox Td-Tomato flox/wt (Dicer cKO) mice. It should be noted that this approach allowed Split-Cre recombinase to be expressed in type 1 aNSCs on the basis of the coincident activity of hGFAP and Prominin1 promoters (Beckervordersandforth et al., 2014) (FIG. 2A). In this way, cell fate in the subgranular zone (SGZ) and granular cell layer (GCL) of the adult hippocampus in vivo was analysed as previously published (Beckervordersandforth et al., 2014).

To check for Dicer ablation in vivo, Td-Tomato+ virtually transduced cells and, as an internal control, uninfected Td-Tomato− (negative) cells were isolated by FACS from the DG of WT and Dicer cKO mice, and Dicer mRNA levels were quantified by qPCR. This quantification confirmed a 70% reduction of Dicer mRNA levels in Td-Tomato+ (positive) cells from Dicer cKO mice, compared to Td-Tomato+ cells from WT mice (FIG. 1B, p=0.0001) and Td-Tomato− cells from both WT and Dicer cKO mice (FIG. 1B, p=0.003).

In order to investigate the survival of the progeny originated from Dicer cKO aNSCs, one month after virus injection, mice were administered with bromodeoxyuridine (BrdU) for 5 consecutive days. Ten days or one month after BrdU administration, the ratio between the SGZ and the GCL of Td-Tomato/BrdU double-positive cells was quantified (FIG. 1A). Despite a slight increase in the ratio of these cells in Dicer cKO and Dicer HT mice (FIG. 1D) at 10 days, this ratio significantly decreased in Dicer cKO mice at one month (FIGS. 1C-D, p=0.006). This result indicates that Dicer depletion impairs the survival of newly born cells in the SGZ/GCL of the adult murine hippocampus in vivo. In addition, when the morphology of Td-Tomato+ cells was analysed, a dramatic reduction was also observed in the number of processes and arborization of Td-Tomato+ Dicer cKO cells in the GCL and molecular layer (ML) of the hippocampus compared to Td-Tomato+ WT cells (FIG. 1C). This finding suggested that Dicer depletion impaired differentiation and maturation of surviving cells.

Subsequently, the role of Dicer in aNSCs' neuronal fate was studied. The ratio of newly born cells co-expressing the Doublecortin marker (DCX, (Gleeson et al., 1999)) for immature neuronal cells or the NeuN marker (Mullen et al., 1992) for post-mitotic neuronal cells in the SGZ/GCL of the adult hippocampus of Dicer WT, HT, and cKO mice was quantified 10 days and 1 month after BrdU administration (as in FIG. 1A). No difference in the expression of DCX and NeuN could be seen between the three Dicer genotypes at 10 days (FIGS. 1F and 1G). However, at one month, the inventors found that 40% of Dicer WT cells also co-expressed DCX, whereas only 10% of Dicer cKO cells or 26% of Dicer HT cells did so (FIG. 1G, WT vs. KO p=0.0012; WT vs. HT p=0.039). Consistently, at the same age, only 20% of Dicer cKO cells co-expressed NeuN, compared to 60% of NeuN+Dicer WT neurons (FIG. 1E left panels and FIG. 1F, p=0.0058). Furthermore, although the ratio of newly born NeuN+neurons increased significantly from 10 days to one month in the SGZ/GCL of Dicer WT mice (FIG. 1F, p=0.0062), no differences were found in the SGZ/GCL of Dicer cKO mice over time (p=0.72). These results indicate that Dicer depletion impaired neuronal differentiation and maturation in the adult murine hippocampus in vivo.

Subsequently, the role of DICER in aNSCs' fate was investigated with regard to astrocyte differentiation, and complementary results were found (FIG. 1E middle and right panels). While about 40% of Dicer WT and HT newly born cells co-expressed the astrocyte marker S100b in the SGZ/GCL both 10 days and one month after BrdU administration, the inventors found that 75% of newly born Dicer cKO cells co-expressed S100b (FIG. 1E right panel and FIG. 1H, p=0.0002). Taken together, these results indicate that Dicer depletion in type 1 aNSCs impairs neurogenesis, but not astrogliogenesis, in the adult hippocampus in vivo.

Figure 2:
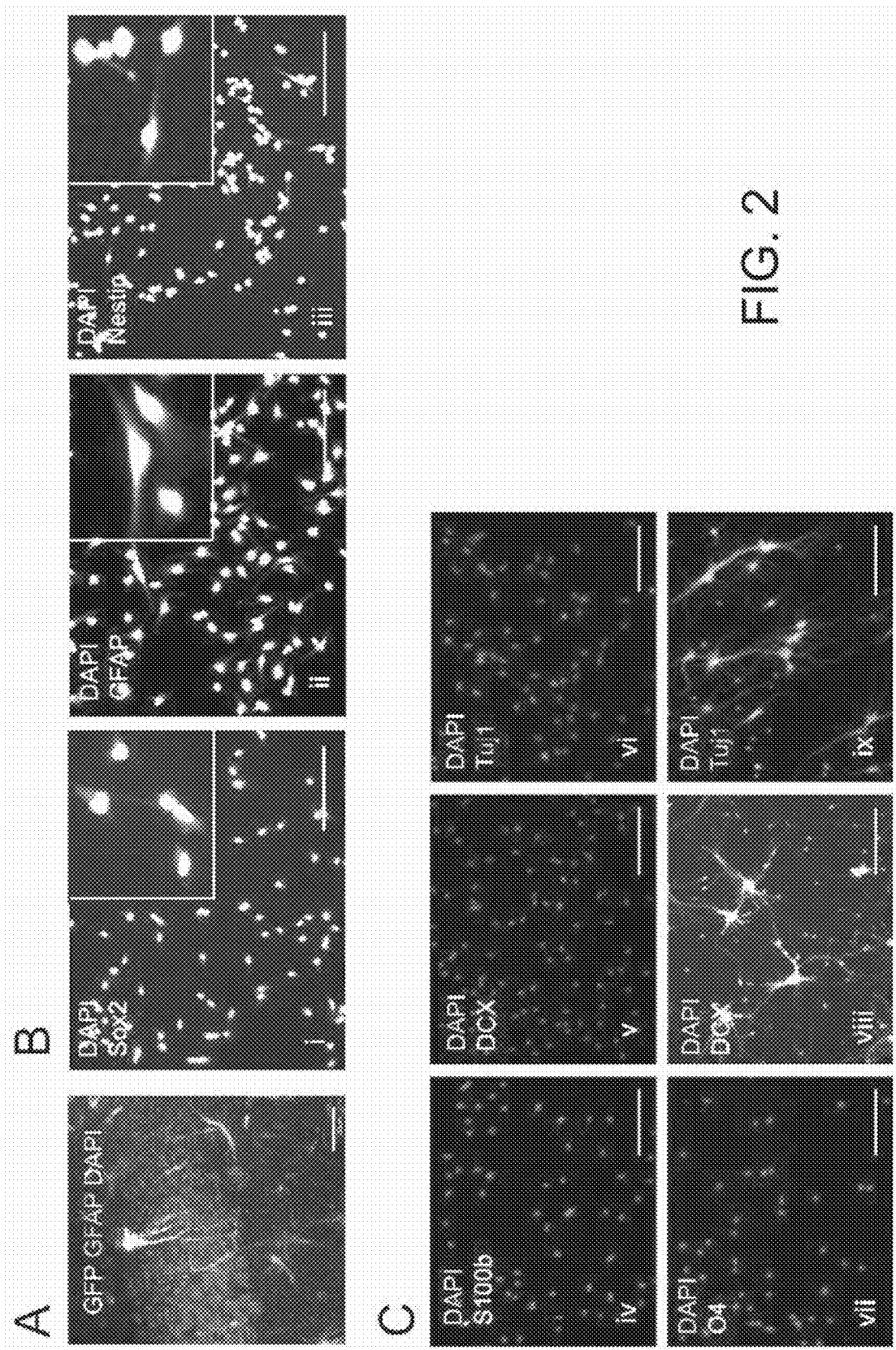
FIG. 2 shows the characterization of the adult neuronal stem cells investigated in vivo and in vitro. A: Radial glial cell (type 1 aNSC) labelled with Split-Cre virus 28 days post injection in CAG CAT reporter mice. Scale bars=20 μm. B: aNSCs cultured in proliferative conditions express stem cell markers such as Sox2 (i), GFAP (ii) and Nestin (iii). C: aNSCs do not express glial differentiation markers such as S100b (iv) and O4 (vii); or neuronal differentiation markers such as DCX (v) and Tuj 1 (vi). Adult murine neurons, used as positive controls, stain for DCX (viii) and Tuj 1 (ix). Scale bar=50 μm.
Figure 3:
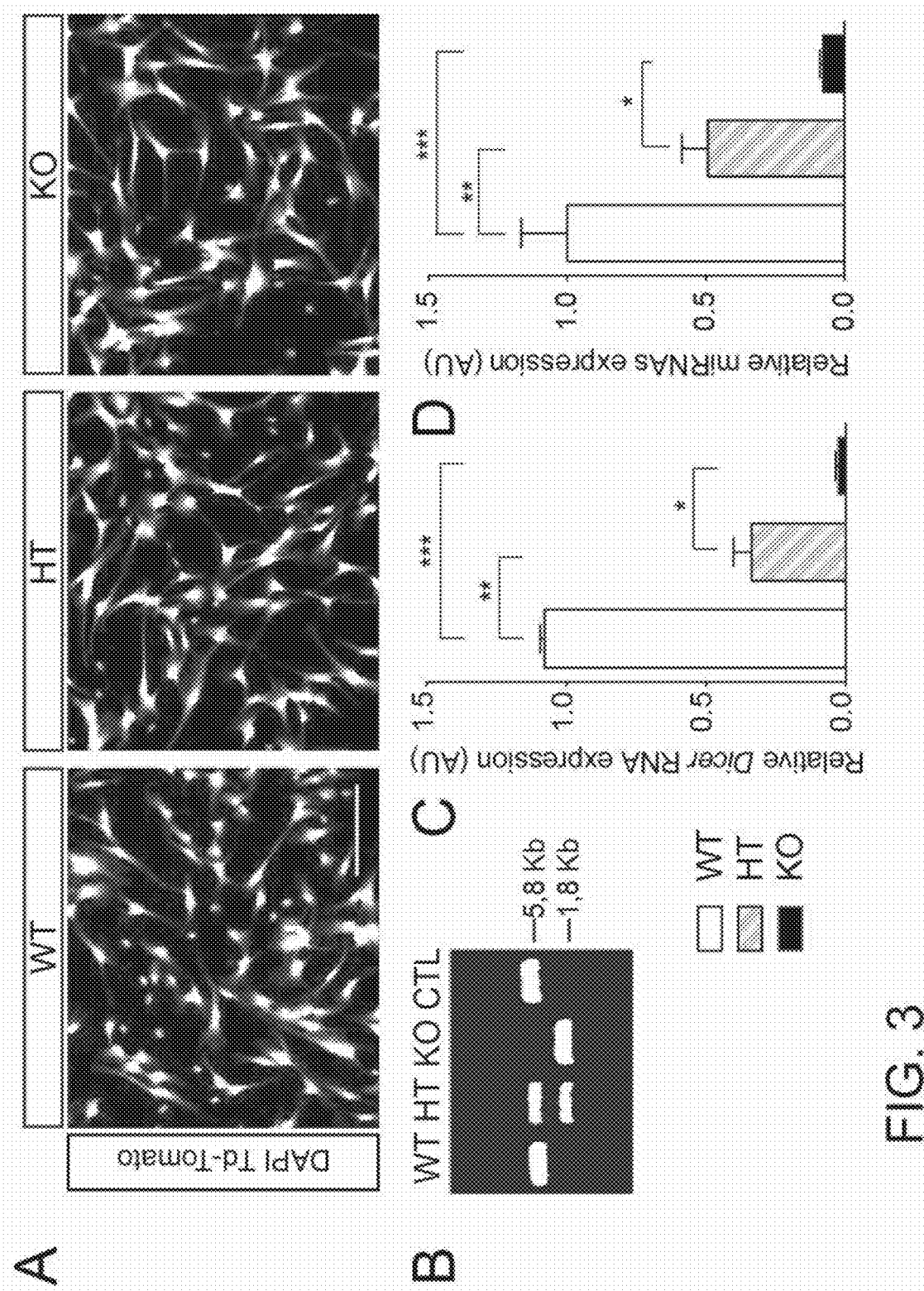
FIG. 3 shows that Dicer and miRNAs are depleted after recombination of Dicer$^{flox}$ allele in hippocampal aNSCs in vitro. A: Representative micrographs showing Td-Tomato+ aNSCs from Dicer$^{wt/wt}$ Td-Tomato$^{flox/wt}$ (WT), Dicer$^{flox/wt}$ Td-Tomato$^{flox/wt}$ (HT) and Dicer$^{flox/flox}$ Td-Tomato$^{flox/wt}$ (KO) mice after nucleofection with Cre-recombinase. B: Treatment with Cre leads to excision of most of the two RNasiIII domains. The three different Dicer genotypes (Dicer$^{wt/wt}$ (WT), Dicer$^{flox/wt}$ (HT) and Dicer$^{flox/flox}$ (KO)) upon Crerecombination can be distinguished by PCR. C: qPCR relative quantification of Dicer mRNA from recombinant aNSCs. D: The average of all miRNAs quantified from recombinant aNSCs. Scale bar=50 μm. Data are expressed as mean+/−SEM. N=3 independent experiments containing 3 replicates. One-way ANOVA Bonferroni post-hoc test *$p<0.05$;  $p<0.01$; *$p<0.001$.

Dicer mRNA and miRNAs are Depleted after Recombination of Dicerflox Allele in Hippocampal aNSCs In Vitro To assess the effect of Dicer ablation in vitro, primary aNSCs were generated from the DG of mice WT, HT and homozygous for Dicer flox allele, that were also heterozygous for the Cre-inducible Td-Tomato allele, as previously described (Babu et al., 2011; Walker and Kempermann, 2014) and these cells were cultured as monolayers (FIG. 2B). Depletion of Dicer was obtained by nucleofection of a plasmid expressing Cre recombinase under the control of a constitutive promoter (pCAGGS-Cre). Cre nucleofection in these cells activated Td-Tomato protein expression (FIG. 3A) and effectively resulted in recombination of the Dicer locus (FIG. 3B). Consistently, the transcript encoding Dicer was reduced to 50% in Dicer HT aNSCs (FIG. 3C, p=0.0082) and was almost completely absent in Dicer cKO aNSCs (FIG. 3C, p=0.0003) as compared to WT aNSCs. Consequently, mature miRNA levels were reduced to 50% in Dicer HT aNSCs (FIG. 3D, p=0.01) and were almost completely absent in Dicer cKO aNSCs (FIG. 3D, residual miRNA levels approximately 7% p<0.0001), compared to WT aNSCs. These results demonstrated that recombination of the Dicer flox allele resulted in efficient depletion of both Dicer transcript and mature miRNAs from hippocampal aNSCs in vitro.

Dicer Ablation does not Affect Proliferation and Expression of Stem Cell Markers, but Increases Apoptosis Upon Differentiation In Vitro.

Figure 4:
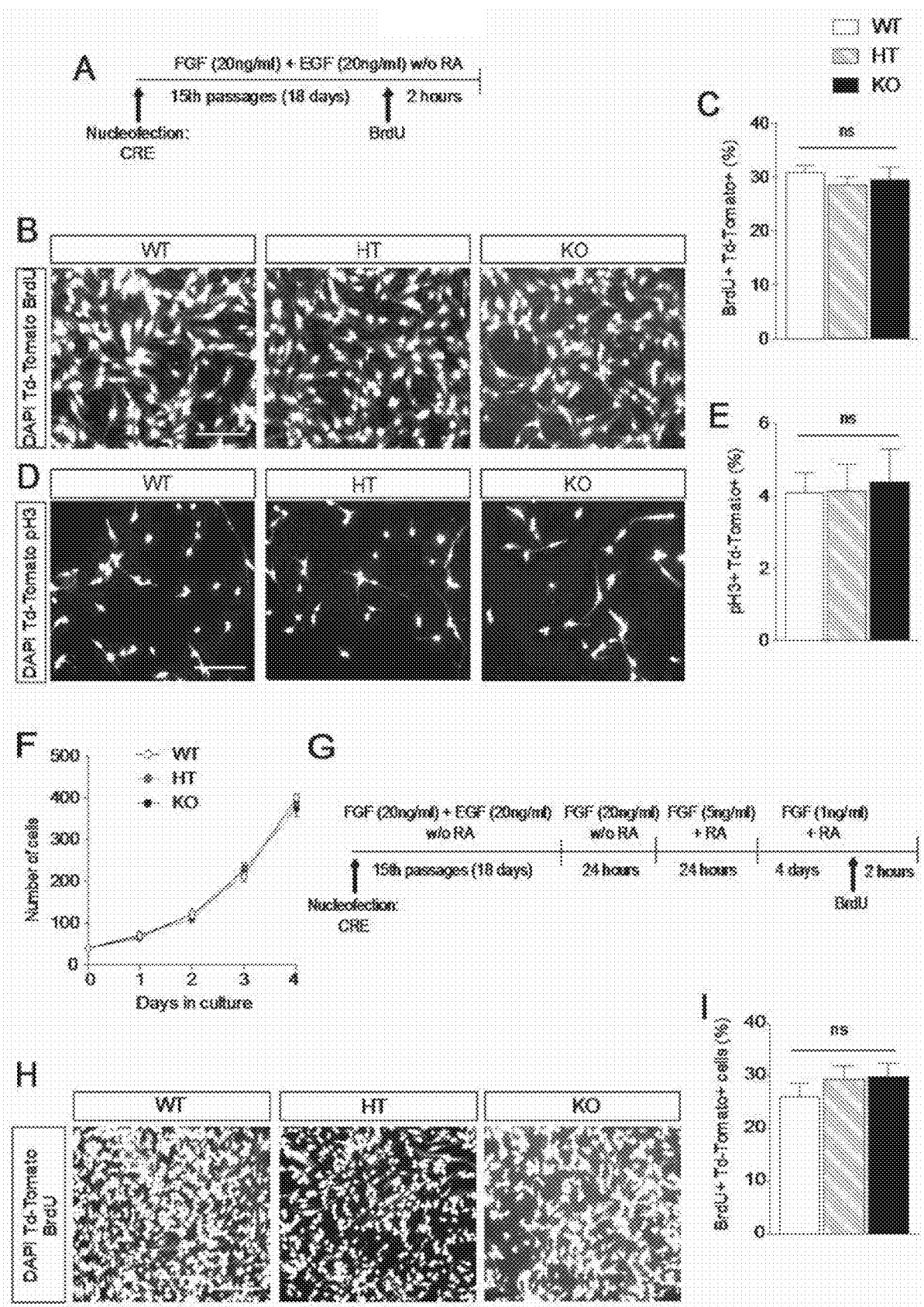
FIG. 4 shows that Dicer/miRNA depletion does not affect aNSC proliferation in vitro. A: Schematic representation of the procedure used to assess proliferation after Dicer ablation. B and D: Representative micrographs showing Td-Tomato+ aNSCs from Dicer$^{wt/wt}$ Td-Tomato$^{flox/wt}$ (WT), Dicer$^{flox/wt}$ Td-Tomato$^{flow/wt}$ (HT) and Dicer$^{flox/flox}$ TdTomato$^{flox/wt}$ (KO) mice expressing BrdU (B and H) or pH3 (D). C and E: Percentage of Td-Tomato+ cells expressing BrdU after a 2-hour pulse (C) or pH3 (E). F: Growth curve representing the aNSC cell numbers per field and the days under proliferation conditions. G: Schematic representation of the procedure used to assess proliferation under differentiation conditions. I: Percentage of Td-Tomato+ cells expressing BrdU. Scale bar=50 μm. Data are expressed as mean+/−SEM. N=3 independent experiments containing 3 replicates. One-way ANOVA Bonferroni post-hoc test.

Despite efficient depletion of Dicer and miRNAs in aNSCs, cells could be maintained in culture under proliferative conditions for at least 18 days in vitro (DIV). No major differences were detected in cell morphology, cell requirements as regards medium exchange, and ratio of these cells compared to Dicer HT and WT aNSCs. Moreover, no differences between genotypes were observed in relation to the percentage of Td-Tomato+ cells incorporating BrdU after a 2-hour pulse (FIGS. 4A-C) or immunopositive for phospho-Histone H3 (PH3 FIGS. 4D-E) under proliferative conditions, or upon growth factor titration (FIGS. 4G-I). Consistently, no differences were observed between genotypes when a growth curve was performed within several days in culture (FIG. 4F). Therefore, the inventors concluded that Dicer/miRNA depletion does not affect aNSC proliferation.

Figure 5:
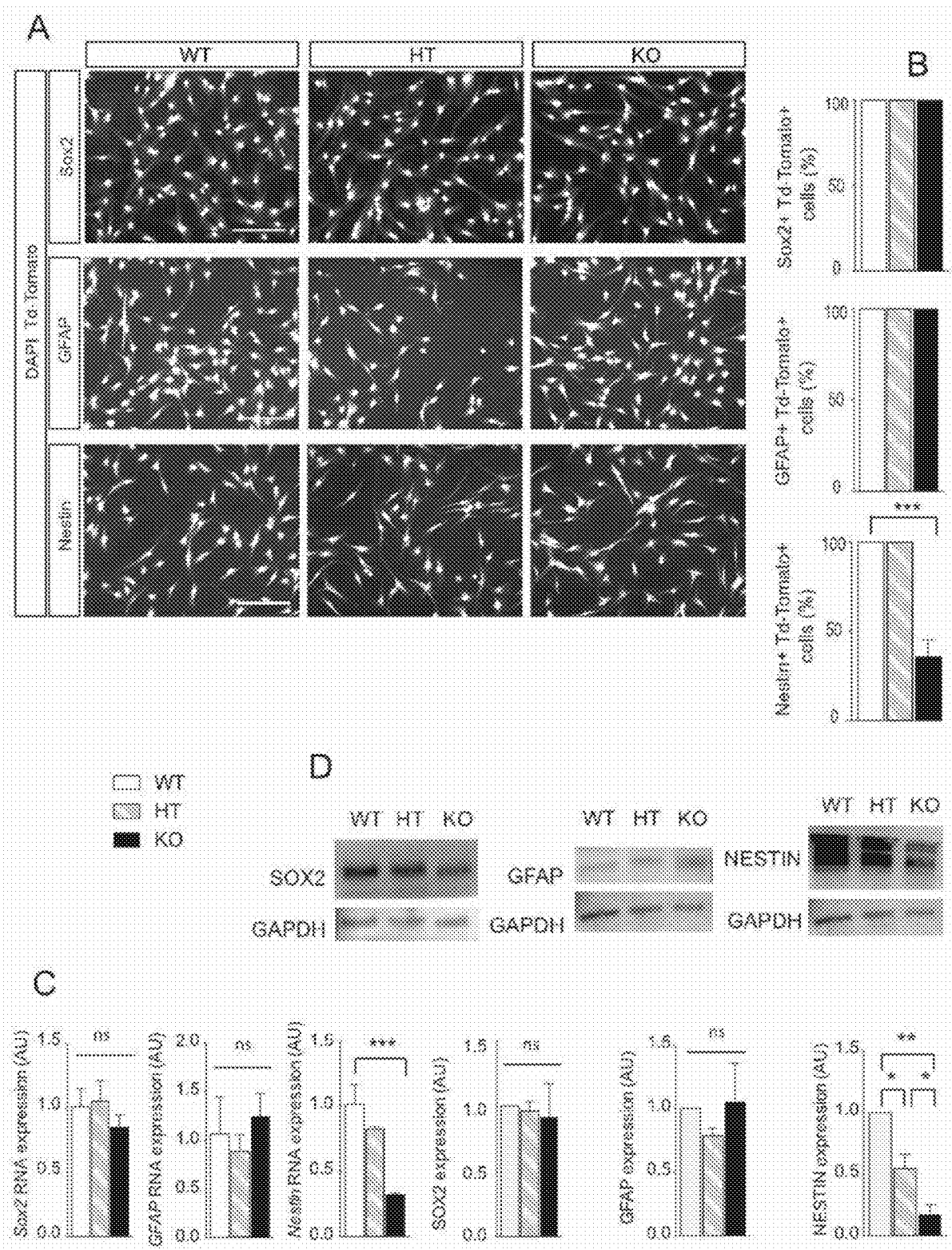
FIG. 5 shows that Dicer/miRNA depletion does not affect the expression of aNSC Sox2 and GFAP markers, but prevents Nestin expression in vitro. A: Representative micrographs showing recombinant (Td-Tomato+) aNSCs from Dicer$^{wt/wt}$ Td-Tomato$^{flox/wt}$ (WT), Dicer$^{flow/wt}$ Td-Tomato$^{flox/wt}$ (HT) and Dicer$^{flox/flox}$ Td-Tomato$^{flox/wt}$ (KO) mice expressing Sox2 (upper panels), GFAP (middle panels) and Nestin (bottom panels). B: Percentage of Td-Tomato+ cells expressing aNSC markers (Sox2, GFAP and Nestin). C: qPCR relative quantification of Sox2, GFAP and Nestin mRNAs from recombinant aNSCs. D: Quantification of SOX2, GFAP and NESTIN proteins from recombinant aNSC cultures. Scale bar=50 μm. Data are expressed as mean+/−SEM. N=3 independent experiments containing 3 replicates. One-way ANOVA Bonferroni post-hoc test. *$p<0.05$;  $p<0.01$; *$p<0.001$.

Subsequently, the inventors raised the question of whether Dicer/miRNA depletion affected the expression of stem cell markers, such as Sox2, GFAP and Nestin, in aNSCs. The inventors found no change in SOX2 or GFAP expression at both the protein and transcript levels (FIG. 5). However, consistent with previous reports, (Andersson et al., 2010), the inventors observed reduced expression of Nestin protein in Dicer cKO aNSCs, and of Nestin mRNA both in Dicer HT aNSCs and cKO aNSCs compared to WT aNSCs (FIGS. 5A-C p=0.0021; FIG. 5D, WT vs. cKO p=0.0053; HT vs. cKO p=0.03). Taken together, these results indicate that Dicer/miRNA depletion does not primarily affect proliferation, requirements relating to medium exchange, and expression of aNSC stem cell markers, with the exception of Nestin.

Figure 6:
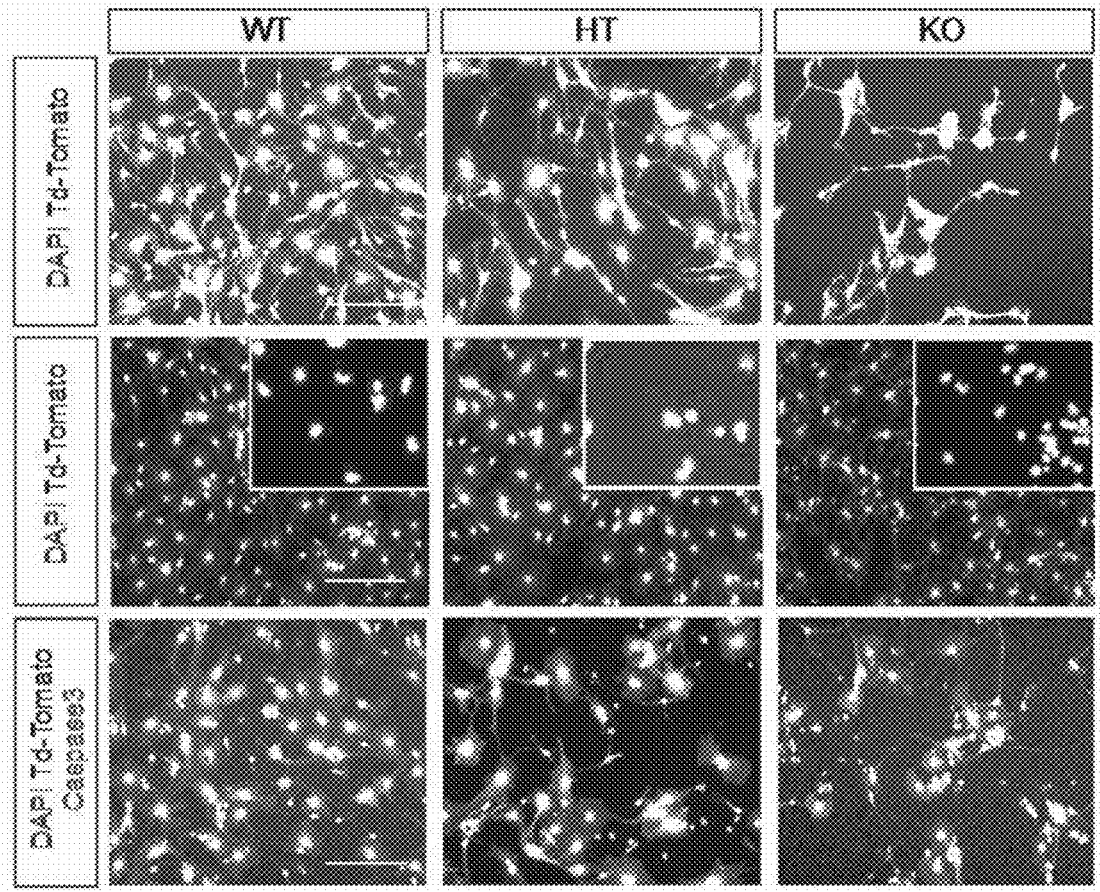
FIG. 6 shows that Dicer/miRNA depletion increases apoptosis of hippocampal aNSCs after differentiation in vitro. A: Schematic representation of the procedure used to assess survival after Dicer ablation. B: Representative micrographs showing Td-Tomato+ aNSCs after 6 DIV, with growth factor titration, from Dicer$^{wt/wt}$ Td-Tomato$^{flox/wt}$ (WT), Dicer$^{flox/wt}$ Td-Tomato$^{flox/wt}$ (HT) and Dicer$^{flox/flox}$ Td-Tomato$^{flox/wt}$ (KO) mice that survived (upper panels), died with pycnotic nuclei (middle panels), and expressed activated caspase 3 (bottom panels). C: Percentage of Td-Tomato+ cells, pycnotic nuclei and Td-Tomato+ cells expressing activated caspase 3 per field normalized to WT aNSCs after 6 DIV. D: qPCR relative quantification of Bcl-2 mRNA from recombinant aNSCs after 6 DIV. Scale bar=50 μm. Data are expressed as mean+/−SEM. N=3 independent experiments containing 3 replicates. One-way ANOVA Bonferroni post-hoc test *$p<0.05$;  $p<0.01$; *$p<0.001$.
Figure 6:
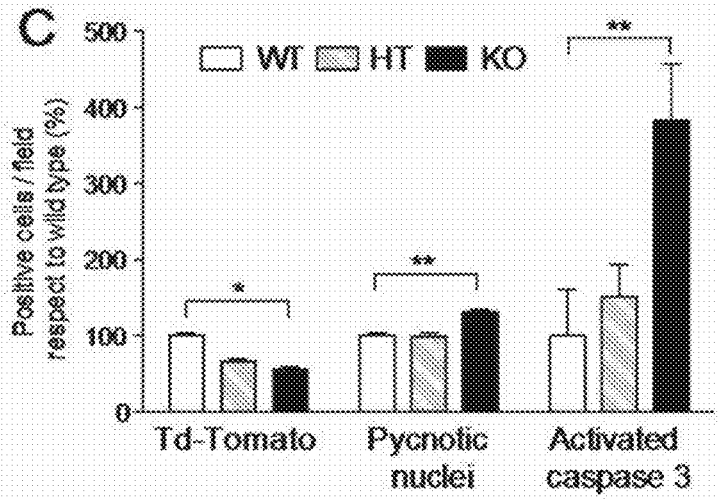
Figure 6:
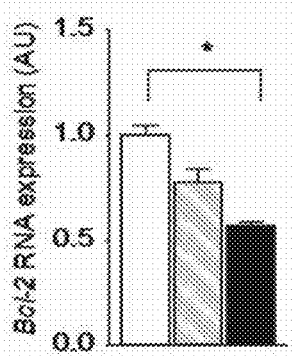

The inventors then investigated survival of Dicer WT, HT and cKO aNSCs after the induction of differentiation. For this purpose, recombinant (Td-Tomato+) Dicer WT, HT and cKO aNSCs were FACS-sorted and cultured under differentiation conditions (FIG. 6A). After 6 DIV, the inventors found a 30% and 50% reduction in the number of Dicer HT and Dicer cKO aNSCs, respectively, compared to Dicer WT aNSCs (FIGS. 6B-C upper panel, WT vs. cKO, p=0.03). Furthermore, the reduced survival of Dicer cKO aNSCs was paralleled by a significant increase in the number of pycnotic nuclei (FIGS. 6B-C middle panel, p=0.0051), expression of the apoptotic marker Active-Caspase 3 (FIGS. 6B-C lower panel, p=0.013), and a significant reduction in the expression of the transcript encoding for the anti-apoptotic protein Blc-2 (FIG. 6D, p=0.04). Therefore, these results indicate that DICER functions are not essential for expansion of aNSCs in vitro, but are required for survival of their progeny upon induction of differentiation, consistently with the in vivo data (FIG. 1).

Figure 7:
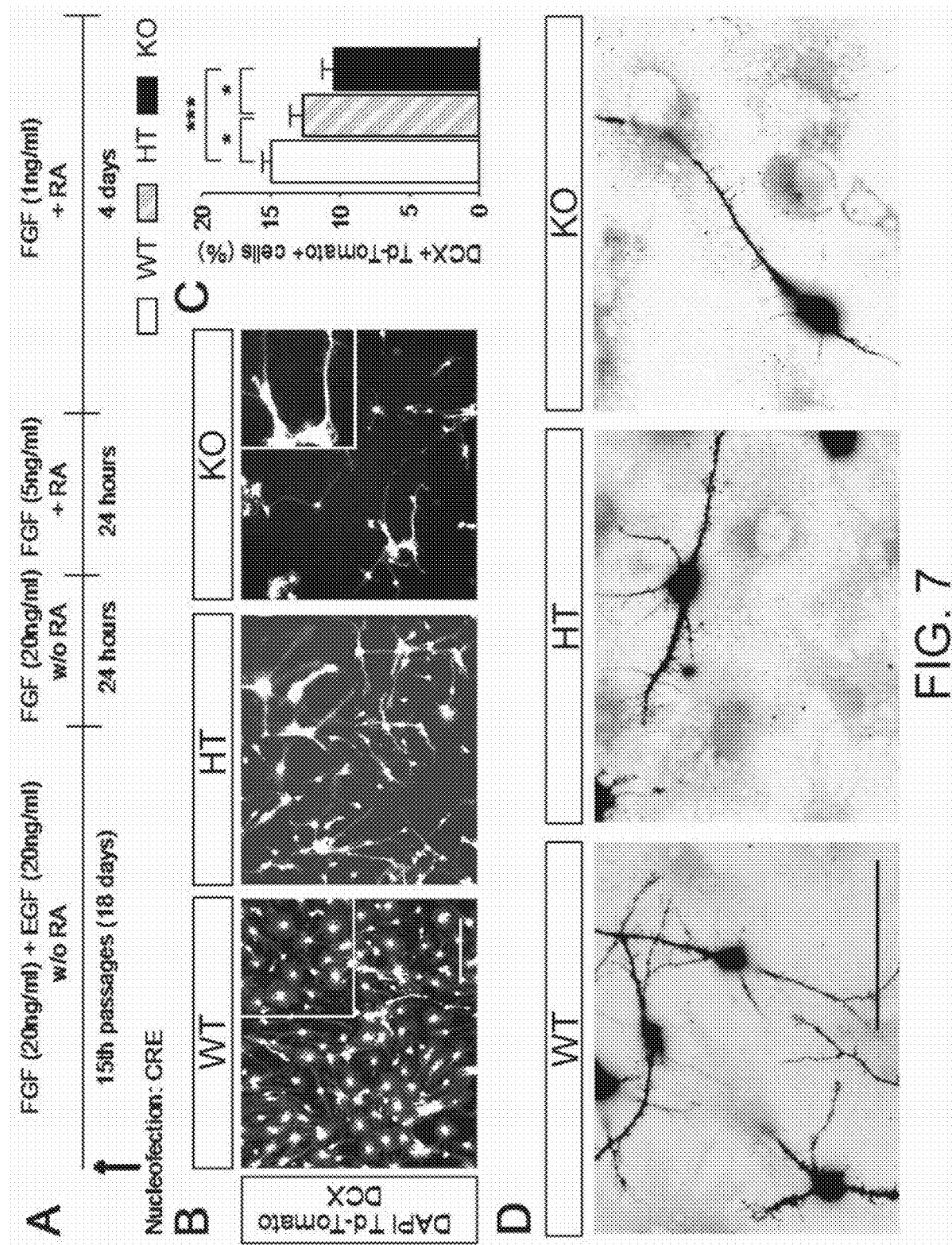
FIG. 7 shows that Dicer/miRNA depletion in aNSCs impairs neurogenesis and neuronal maturation in vitro. A: Schematic representation of the procedure used to assess neuronal differentiation after Dicer ablation. B: Representative micrographs showing recombinant Td-Tomato+ aNSCs from Dicer$^{wt/wt}$ Td-Tomato$^{flox/wt}$ (WT), Dicer$^{flox/wt}$ TdTomato$^{flox/wt}$ (HT) and Dicer$^{flox/flox}$ Td-Tomato$^{flox/wt}$ (KO) mice after 6 DIV, with growth factor titration, expressing doublecortin (DCX). C: Percentage of Td-Tomato+ cells expressing doublecortin (DCX). D: Representative micrographs showing dendritic morphology of newly formed immature neurons expressing DCX. Scale bar=50 μm. Data are expressed as mean+/−SEM. N=3 independent experiments containing 3 replicates. One-way ANOVA Bonferroni post-hoc test *$p<0.05$; ***$p<0.001$.

Dicer/miRNA Depletion in aNSCs Impairs Neurogenesis, but not Astrogliogenesis In Vitro In vivo data obtained by the present inventors suggest that Dicer depletion in aNSCs impairs neurogenesis, but not astrogliogenesis, in the adult murine hippocampus (FIG. 1). Therefore, the inventors isolated recombinant (Td-Tomato+) Dicer WT, HT and cKO aNCSs and examined neurogenesis and neuronal maturation upon differentiation in vitro (FIG. 7A). The inventors found that Dicer HT and cKO aNSCs generated significantly less DCX+ cells compared to WT aNSCs (FIGS. 7B-C, DCX+ ~12% in Dicer HT p=0.04; ~9% in Dicer cKO p=0.0013). In addition, the inventors observed a reduction in neurite numbers, branching and spines in DCX+ Dicer cKO cells compared to Dicer WT and HT cells (FIG. 7D).

Figure 8:
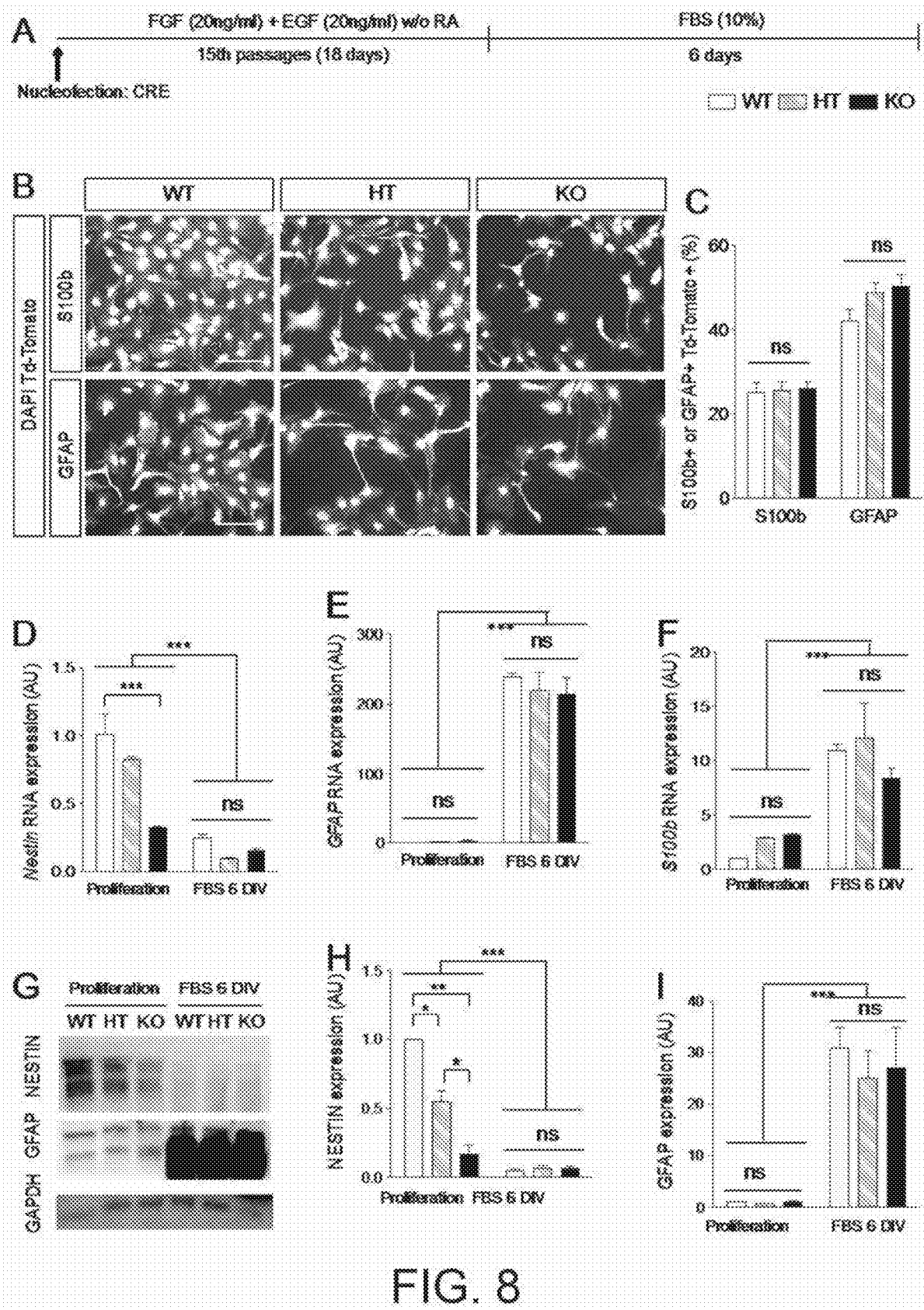
FIG. 8 shows that Dicer/miRNA depletion does not affect astrocyte differentiation of aNSCs in vitro. A: Schematic representation of the procedure used to assess astrocyte differentiation of recombinant aNSCs with 10% FBS. B: Representative micrographs showing recombinant Td-Tomato+ aNSCs from Dicer$^{wt/wt}$ Td-Tomato$^{flox/wt}$ (WT), Dicer$^{flox/wt}$ Td-Tomato$^{flox/wt}$ (HT) and Dicer$^{flox/flox}$ Td-Tomato$^{flox/wt}$ (KO) mice after 6 DIV with 10% FBS, expressing S100b (upper panels) and GFAP (bottom panels). C: Percentage of Td-Tomato+ cells expressing astrocyte markers (GFAP and S100b). D-F: qPCR relative quantification of Nestin, GFAP and S100b mRNAs from recombinant aNSCs after 6 DIV. G-I: Quantification of NESTIN and GFAP proteins in recombinant aNSCs after 6 DIV with 10% FBS. Scale bar=50 μm. Data are expressed as mean+/−SEM. N=3 independent experiments containing 3 replicates. One-way ANOVA Bonferroni post-hoc test *$p<0.05$;  $p<0.01$; *$p<0.001$.
Figure 12:
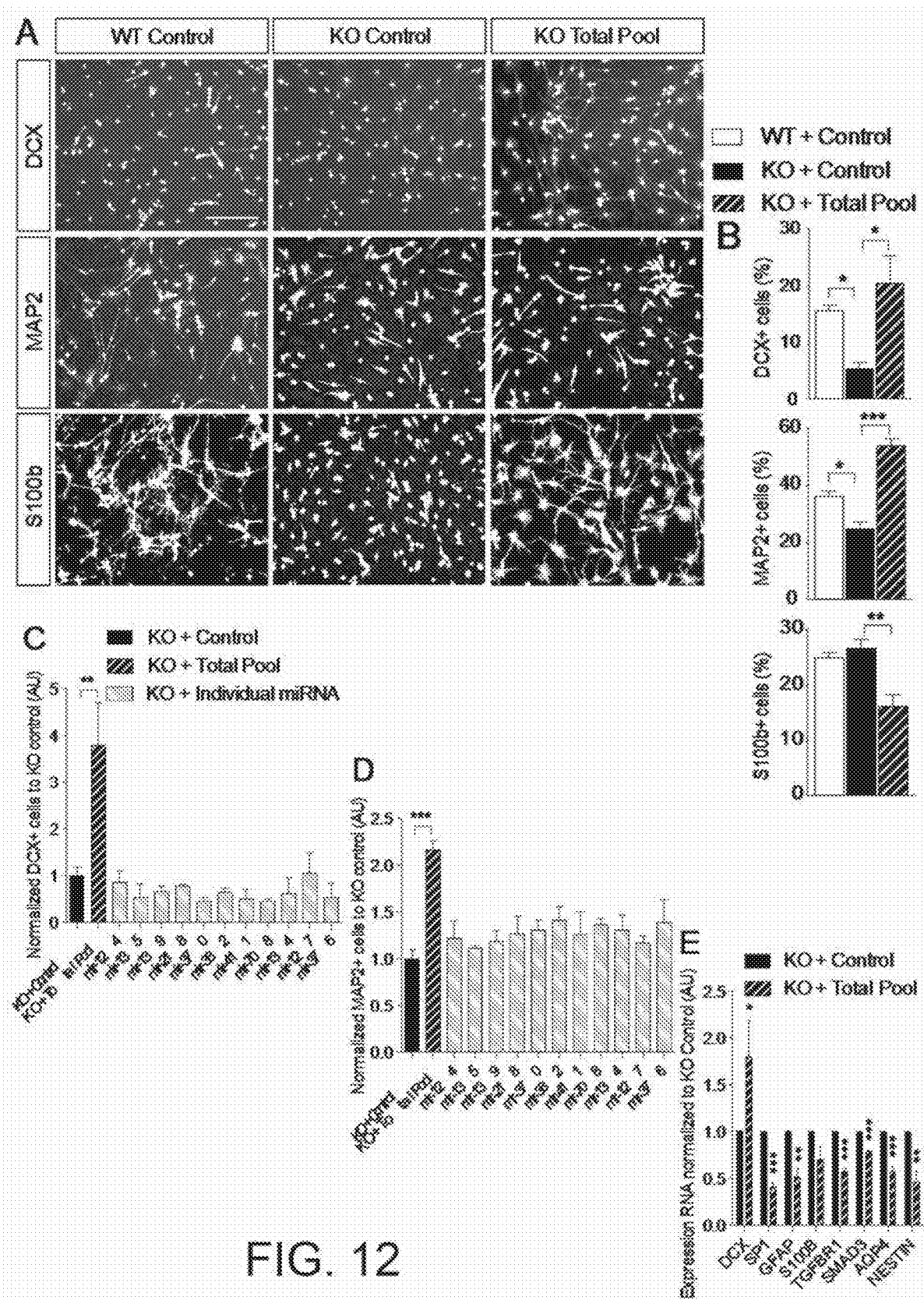
FIG. 12 shows that a pool of eleven miRNAs synergistically rescues Dicer-cKO impairment of adult neurogenesis, at the expense of gliogenesis in vitro. A: Representative micrographs showing aNSCs from WT or Dicer$^{flox/flox}$ Td-Tomato$^{flox/wt}$ (KO) mice transfected with 250 nM scrambled RNA or with a pool of the eleven selected miRNAs (Total Pool), after 6 DIV with removal of growth factors, expressing doublecortin (DCX) (upper panel), MAP2 (middle panel) and S100b (bottom panel). B: Percentage of DCX-, MAP2- and S100b-positive aNSCs compared to DAPI-positive cells in WT and KO aNSCs transfected with 250 nM scrambled RNA or 250 nM Total Pool (25 nM of each miRNA). C-D: Ratio of KO aNSCs expressing DCX (C) and MAP2 (D) upon transfection of individual miRNAs (225 nM scrambled RNA+25 nM specific miRNA) compared to the KO control. E: qPCR mRNA quantification from recombinant KO aNSCs after 6 DIV. Scale bar=50 μm. Data are expressed as mean+/−SEM. N=3 independent experiments containing 3 replicates. One-way ANOVA Bonferroni post-hoc test *$p<0.05$;  $p<0.01$; *$p<0.001$.

Next, the inventors investigated astrogliogenesis in recombinant (Td-Tomato+) Dicer WT, HT and cKO aNCSs after differentiation (FIG. 12A) and found no differences between the three Dicer genotypes (FIG. 12B, below). Subsequently, the inventors induced differentiation into astrocytes with 10% fetal serum for 6 DIV (FIG. 8A) (Wang et al., 2011). Again, no difference was observed in the ratio of cells expressing the astrocyte markers GFAP and S100b between the three Dicer genotypes (FIGS. 8B-C). These data were supported by a parallel decrease in the expression of the aNSC marker Nestin, at both the protein and mRNA levels (FIGS. 8D-H), and by a dramatic increase in the expression of astrocyte markers such as GFAP and S100b (FIGS. 8E-H) in the three Dicer genotypes. These in vitro findings are consistent with in vivo evidence (FIG. 1) and indicate that DICER functions are essential for aNSC differentiation towards neurogenesis and neuronal maturation, but not astrogliogenesis.

Figure 9:
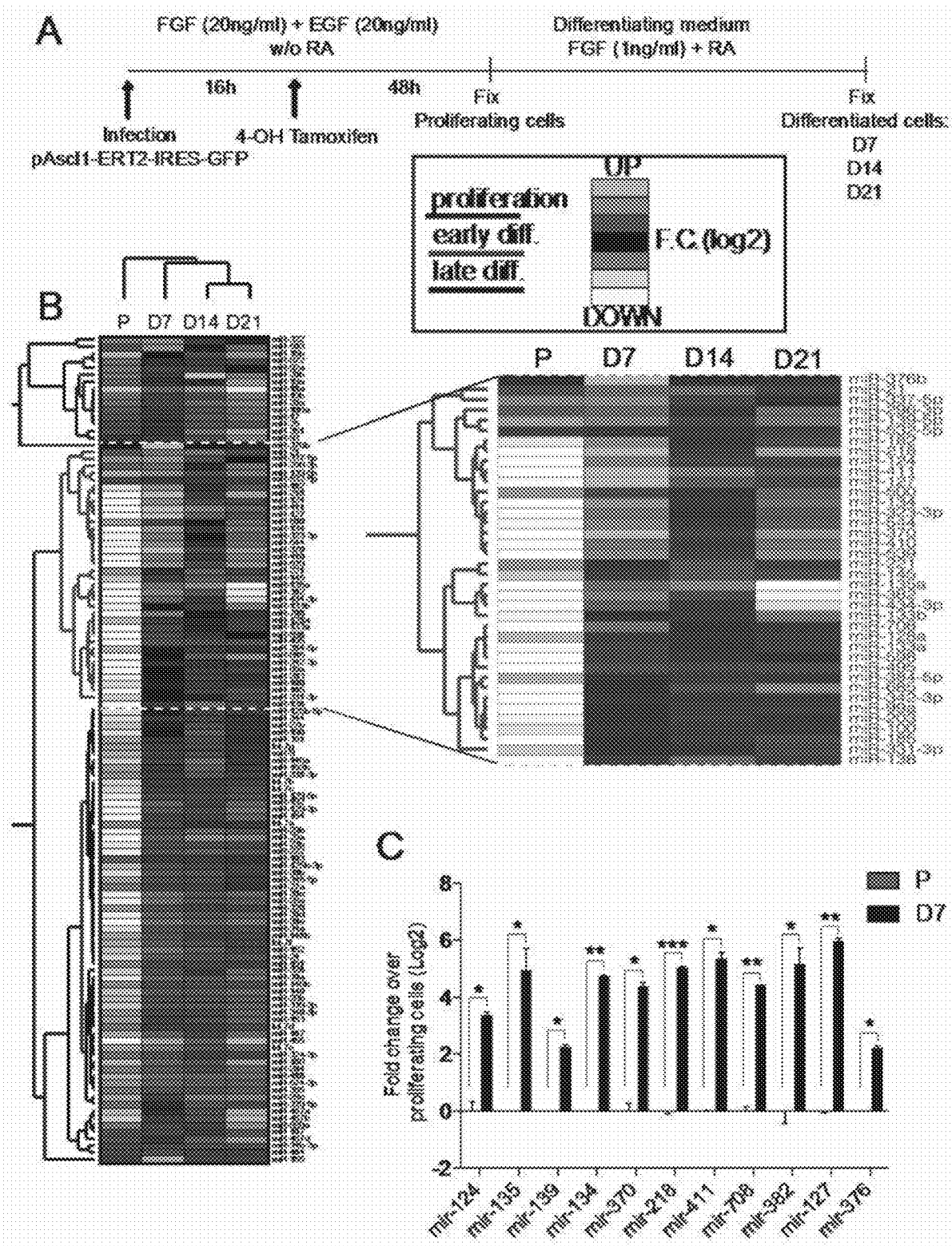
FIG. 9 shows miRNA expression profiles during neuronal differentiation of aNSCs in vitro. A: Schematic representation for inducing neuronal differentiation of hippocampal aNSCs by using an inducible retrovirus expressing Ascl1 (Ascl1-ERT2-IRES-GFP). Cells were harvested during proliferation or differentiation after 7 (D7), 14 (D14) and 21 (D21) DIV. B: Heatmap representing the set of miRNAs dynamically regulated upon neuronal differentiation during 7, 14 and 21 DIV. Red: High expression. Green: Low expression. C: Fold change of a few selected miRNAs during differentiation over proliferating cells. Data are expressed as mean+/−SEM. N=2 independent experiments containing 3 replicates. Paired t-test *$p<0.05$.
Figure 10:
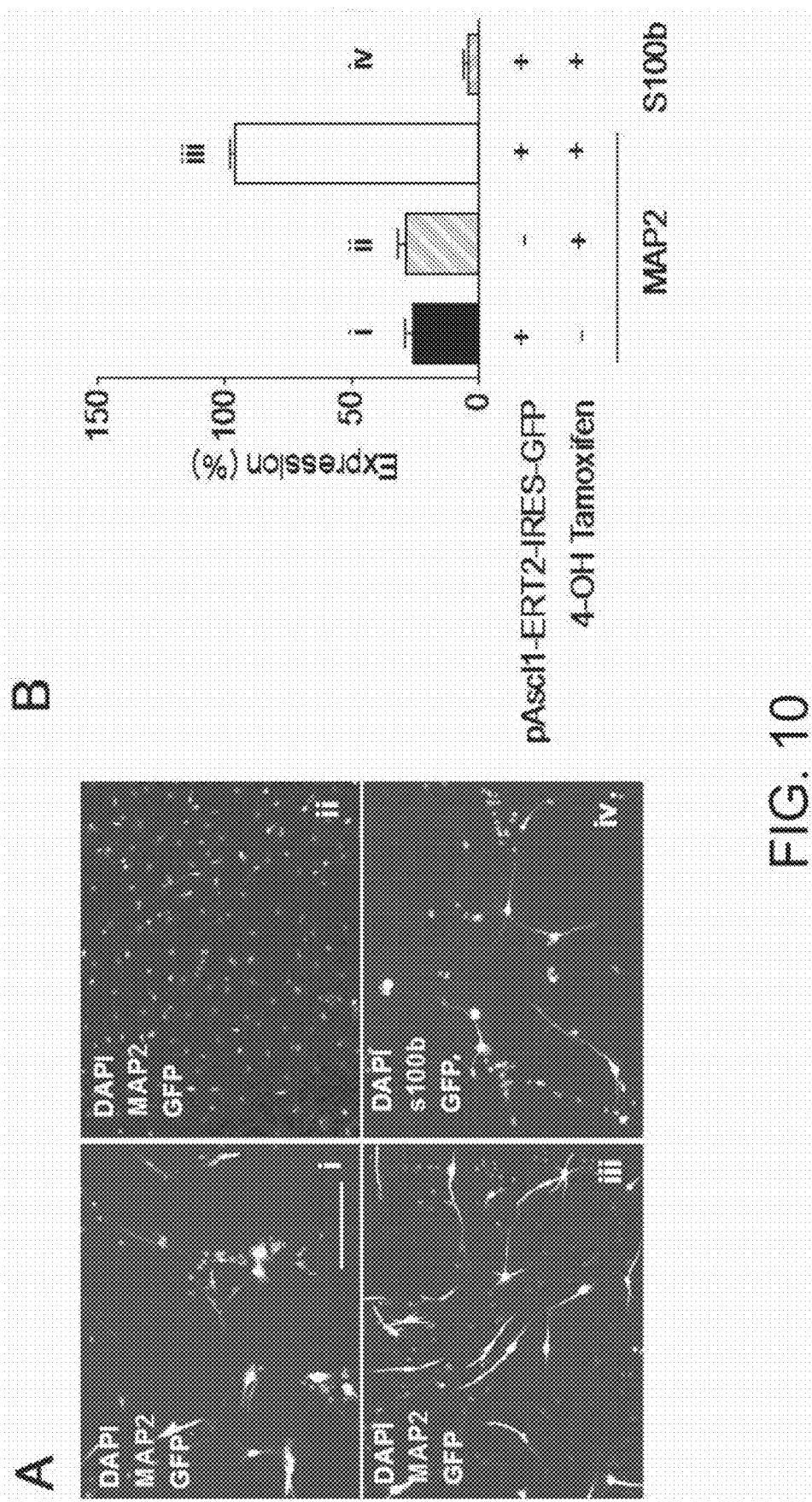
FIG. 10 shows differentiation of hippocampal aNSCs by using an inducible retrovirus expressing Ascl1 (Ascl1-ERT2-IRES-GFP). After 6 DIV, upon 4-OH tamoxifen administration, 95% of infected cells (GFP+) differentiated into neurons. A: Representative micrographs showing neuronal differentiation efficiency upon Ascl1 expression in hippocampal aNSCs at 6 DIV. B: Percentage of cells expressing MAP2 or S100b compared to infected GFP+ (i, iii and iv) or DAPI+ (ii) cells under different conditions at 6 DIV. Scale bar=50 μm. Data are expressed as mean+/−SEM. N=3 independent experiments containing 3 replicates.
Figure 11:
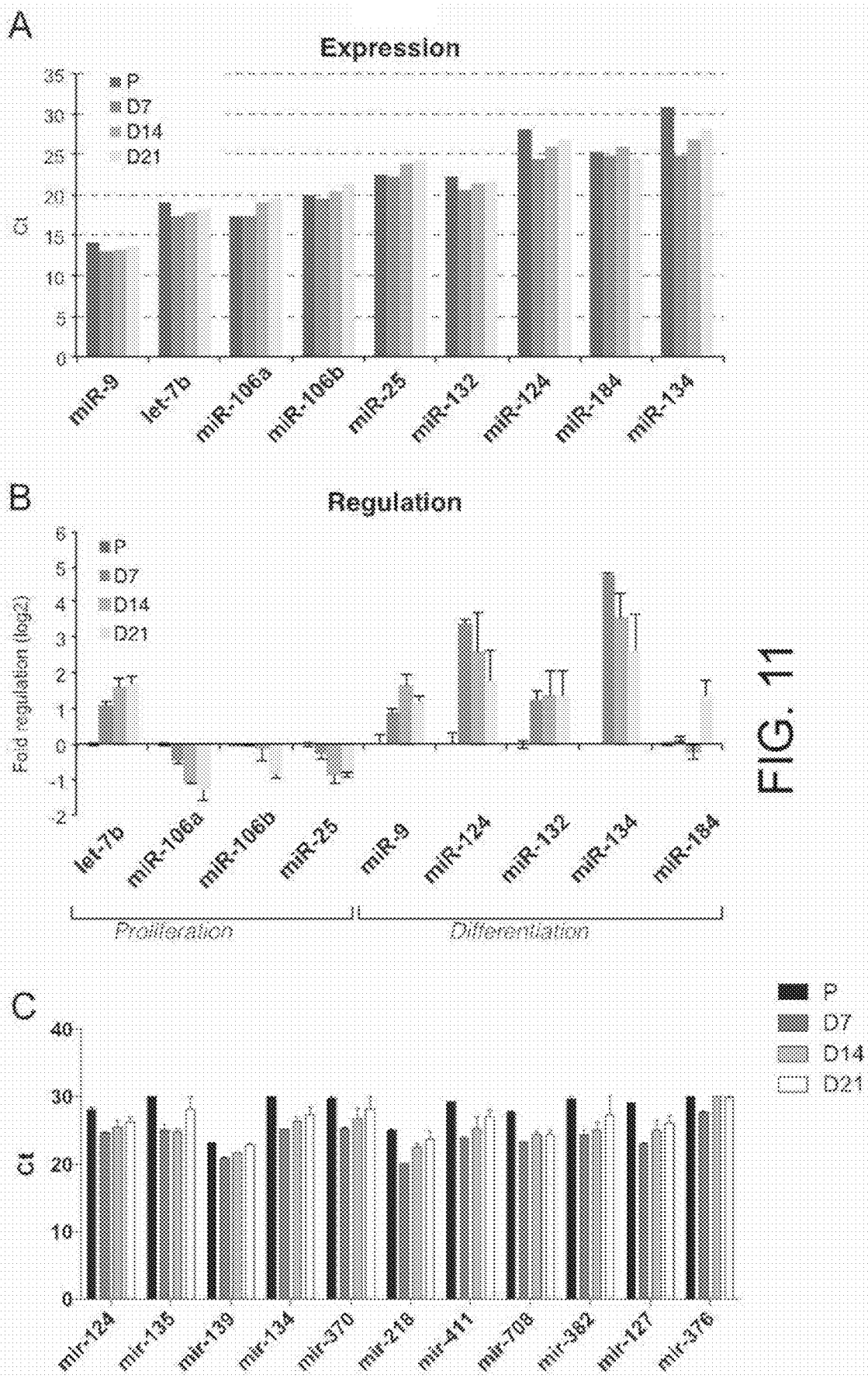
FIG. 11 shows neurogenesis-induced expression of miRNAs. A: Expression levels of miRNAs known to be involved in neurogenesis as reported by Schouten et al., 2012. B: Fold regulation of known miRNAs during neuronal differentiation. C: Expression levels of a few selected miRNAs in this study during proliferation (P) or differentiation after 7 (D7), 14 (D14) and 21 (D21) DIV. Data are expressed as mean+/−SEM.

A Pool of Eleven miRNAs Determines aNSC Neurogenic Fate at the Expense of Astrogliogenesis The inventors sought to clarify whether DICER-dependent miRNAs or other RNA interference (RNAi)-related functions of DICER are involved in the control of adult hippocampal neurogenesis. First, the inventors analysed the dynamics of miRNA expressions in WT aNSCs under proliferative conditions, and at 7, 14 and 21 DIV after neuronal differentiation, by virally-induced Ascl1 expression (Braun et al., 2013) (FIG. 9A). This approach enabled them to obtain 95% MAP2+ neurons after viral infection of aNSCs (FIG. 10). 335 mature miRNAs were detected in these cells by qRT-PCR, which were classified into three groups according to their expression levels and dynamics under proliferation, early neuronal differentiation (7 DIV), and late neuronal differentiation (14 and 21 DIV) (FIG. 9B). miRNAs known to be involved in proliferation or neuronal differentiation were dynamically regulated (FIGS. 11A-B, (Schouten et al., 2012), thus supporting the validity of the inventors' approach.

The inventors hypothesised that miRNAs whose expression was associated with the early stages of neurogenesis could counteract DICER-dependent neurogenesis impairment. Therefore, the inventors focused on a group of 11 miRNAs showing a preferential enrichment (fold change: Log>2) and high expression levels (Ct values <25) during early neuronal differentiation (7 DIV): miR-376b-3p, 139-5p, 218-5p, 411-5p, 127-3p, 134-5p, 370-3p, 135a-5p, 382-5p, 708-5p, 124-3p (FIG. 9B, magnification, and FIG. 9C). aNSCs were transfected with a pool containing the 11 miRNAs (hereinafter referred to as "total pool", SEQ ID NO:1-11), or control miRNAs in Dicer cKO aNSCs. Six days after transfection, the inventors found that the total pool, but not the control miRNAs, induced a twofold induction of the neuronal differentiation in Dicer cKO cells, as shown by expression of the neuronal markers DCX (FIGS. 12A-B, p=0.012; FIG. 12E for mRNA quantification, p=0.03) and MAP2 (FIGS. 12A-B, p=0.0001), thereby rescuing the Dicer cKO impairment of neurogenesis to WT levels. Instead, when administered individually, none of the 11 miRNAs was able to rescue neurogenesis in Dicer cKO aNSCs compared to the total pool (FIGS. 12C-D).

To check whether these miRNAs, besides stimulating neurogenesis, can also repress astrogliogenesis, the inventors analysed the expression of S100b markers in Dicer cKO aNSCs after transfection with the total pool or the control miRNAs. They found reduced differentiation into astrocytes, as shown by expression of S100b (FIGS. 12A-B, p=0.003) and GFAP-encoding mRNA (FIG. 12E, p=0.0019), which suggests that these miRNAs are involved in the control of the switching of aNSCs' fate between neurons and astrocytes.

Figure 13:
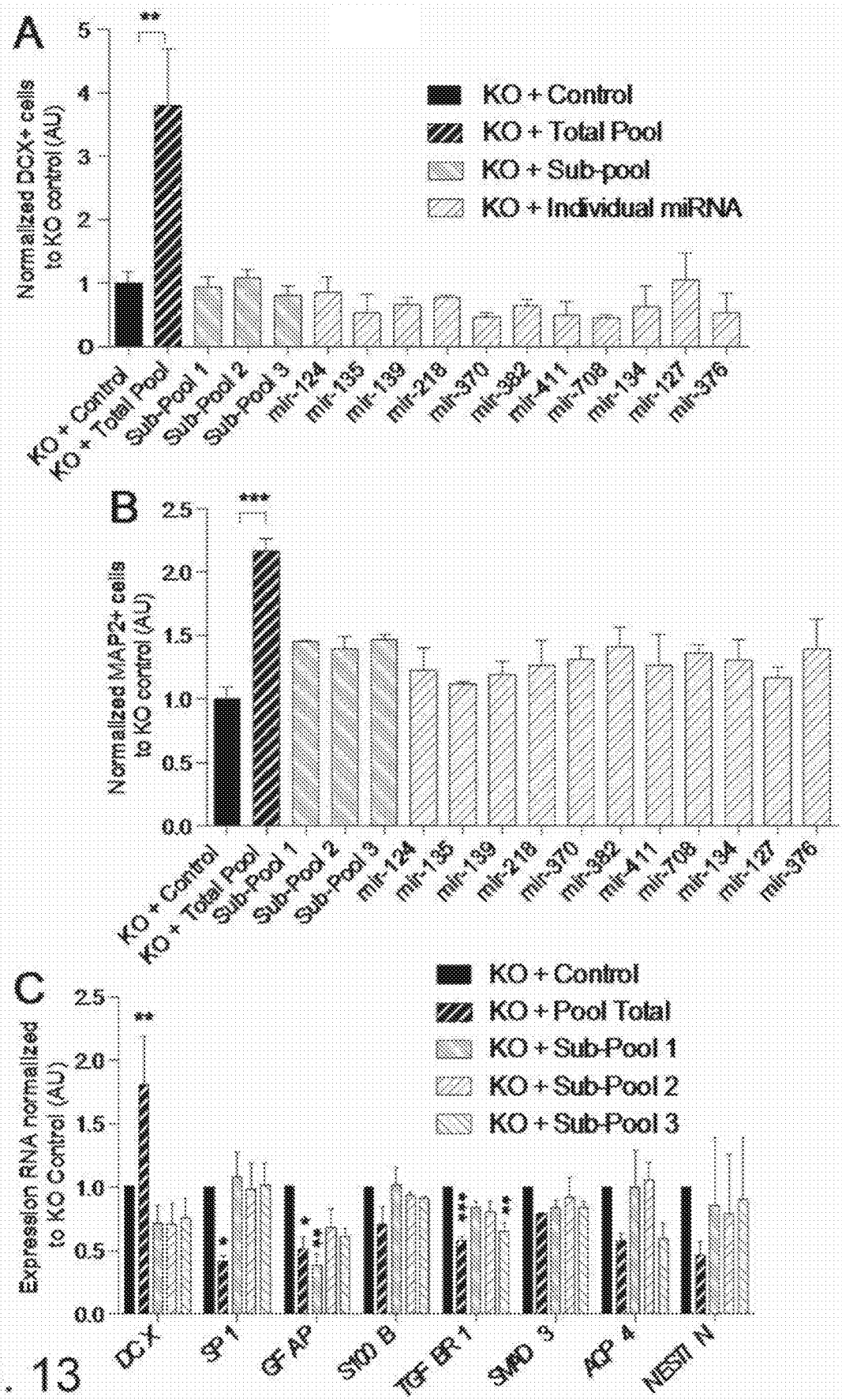
FIG. 13 shows that specific miRNA sub-pools do not rescue neuronal differentiation in Dicer cKO aNSCs in vitro. A-B: Ratio of Dicer KO aNSCs expressing DCX (A) and MAP2 (B) upon transfection with specific miRNA sub-pools compared to the KO control after 6 DIV. C: qPCR mRNA quantification from Dicer KO aNSCs transfected after 6 DIV. Dicer KO aNSCs were transfected with 250 nM scrambled RNA, 250 nM Total Pool (25 nM of each miRNA), 250 nM Sub-Pool 1 (220 nM scrambled RNA+25 nM mir-124-3p+25 nM mir-135a-5p), 250 nM Sub-Pool 2 (75 nM scrambled RNA+25 nM mir-139-5p+25 nM mir-218-5p+25 nM mir-411-5p+25 nM mir-134-5p+25 nM mir-370-3p+25 nM mir-382-5p+25 nM mir-708-5p), 250 nM Sub-Pool 3 (220 nM scrambled RNA+25 nM mir-127-3p+25 nM miR-376b-3p), or with each miRNA alone (225 nM scrambled RNA+25 nM specific miRNA). Data are expressed as mean+/−SEM. N=3 independent experiments containing 3 replicates. One-way ANOVA Bonferroni post-hoc test  $p<0.01$; *$p<0.001$.

In addition, the inventors also analysed the effect of specific miRNA sub-pools, and compared their effect with that of the total pool. However, none of the sub-pools rescued the impaired neuronal differentiation of Dicer-cKO aNSCs (FIG. 13, Sub-Pool 1; Sub-Pool 2 and Sub-Pool 3). These results demonstrate that 11 miRNAs are sufficient and necessary to support neuronal fate determination in hippocampal aNSCs by synergic effect, at the expense of gliogenesis.

Based on this evidence, the inventors also carried out an in silico analysis to identify potential targets for the 11 miRNAs that might be involved in the control of differentiation into astrocytes or neurons in aNSCs. miRWalk 2.0 software was used with highly restrictive parameters, and a very large fraction (37%, i.e. 1817 out of 4929) of predicted targets was found to be shared by at least two of the 11 miRNAs. Interestingly, many of these genes were previously shown to be expressed in developing astrocytes or neurons (Cahoy et al., 2008). The inventors then hypothesized that the 11 miRNAs can achieve their proneurogenic effect by simultaneously suppressing pro-gliogenic and anti-neurogenic genes. In order to test this possibility, the inventors manually selected genes that were predicted targets for at least 5 of the 11 miRNAs, and measured their expression levels in Dicer cKO aNSCs after transfection with the control miRNAs, total pool or sub-pools. Indeed, after transfection with the total pool (FIG. 12E), but not after transfection with the sub-pools (FIG. 13C), a significant reduction in expression of negative regulators of neuronal differentiation, such as SP1 (p=0.0001), or astrocyte differentiation, such as Aqp4 (p=0.0002), Smad3 (p=0.0001) and Tgfbr1 (p=0.0001), was observed after neurogenesis rescue in Dicer cKO aNSCs (FIG. 12E). These results confirm the hypothesis that the 11 miRNAs determine the neurogenic fate by simultaneous suppression of pro-gliogenic and anti-neurogenic genes.

Discussion

The study carried out by the present inventors showed for the first time that in the adult hippocampus a set of 11 miRNAs is critical for differentiation of aNSCs into neurons, at the expense of astrogliogenesis. Remarkably, these miRNAs rescued a previously impaired neurogenesis to normal levels in Dicer-cKO aNSCs only when administered as a pool, while administration of individual miRNAs had no effect. Therefore, the studies carried out by the present inventors provided experimental evidence for the emerging concept of miRNA cooperativity that, by synergetically activating gene regulation mechanisms, affects aNSCs' differentiation programs.

Adult neurogenesis is a highly conserved process among vertebrates (Gage and Temple, 2013), but the mechanisms underlying the control of proper acquisition of the neurogenic vs. astrogliogenic fate were still to be elucidated (Bonaguidi et al., 2012; Kempermann, 2011). By means of the studies carried out on Type I aNSCs in vivo and in vitro, the present inventors demonstrated that Dicer ablation in aNSCs impairs neurogenesis, but not astrogliogenesis. Therefore, the results obtained reveal that miRNAs represent a new level of regulation necessary to sustain the neurogenic lineage and prevent astrogliogenesis in the adult hippocampus.

Moreover, the studies performed by the inventors provide evidence that eleven miRNAs are capable of rescuing neurogenesis after Dicer ablation in aNSCs, demonstrating that the miRNAs are key neurogenesis regulators in aNSCs. Furthermore, the in vitro model used by the present inventors allowed specific miRNAs involved in early determination of aNSCs' neuronal fate to be functionally dissected. Indeed, the inventors found out that a pool of eleven miRNAs was sufficient and necessary to rescue neurogenesis in Dicer cKO aNSCs to normal (wild-type) levels.

Example 2: Therapeutic Application in Glioblastoma

U87MG (ATCC HTB-14) is a commonly studied grade IV glioma cell line that has been analysed in at least 1,700 publications over 4 decades and was shown to induce malignant gliomas upon intracerebral injection in nude mice. This cell line was obtained from a male 44-year-old cancer patient at Stage IV (see also ATCC, HTB-15 and ATCC HTB-16) from J. Ponten and associate professors between 1966 and 1969. Analysis of the genomic sequence of U87MG provides a yet unparalleled level of mutational resolution compared to any other cell line, revealing 512 genes with homozygous mutations, including 154 SNVs (single nucleotide variations), 178 small indels, 145 large microdeletions and 35 interchromosomal translocations.

Methods

Human primary glioblastoma cell line U87MG was plated at $1.2*10E4$ cells/cm$^2$ in culture medium for 24 hours. Three medium conditions were tested: i) EMEM medium supplemented with 10% FBS; ii) EMEM medium without FBS; and (iii) NB supplemented with retinoic acid. The next day, cells were transfected with 250 nM mimics (negative control, CN-001000-01-05; Dharmacon); or with a pool of the eleven miRNAs of the invention by using Lipofectamine 2000 (Thermofisher) following the manufacturer's instructions. 24 hours after transfection, the cells were detached with trypsin, counted and plated at an appropriate density suitable for spheroids. Spheroids containing approximately 500 cells were transferred to 3D collagen gels and incubated at 37° C. and 5% $CO_2$ in a humidified chamber. Images were obtained 1, 4 and 6 days after inclusion of the spheroids in the gel.

Results

Figure 14:
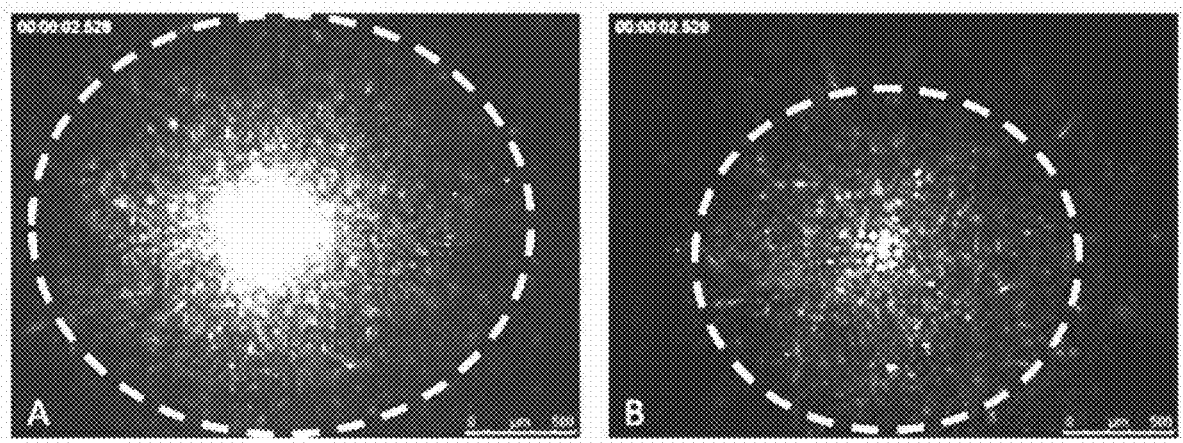
FIG. 14 shows U87MG spheroids cultured in 3D collagen gel after 6 days of incubation with EMEM plus 10% FBS. A: GFP+U87MG transfected with control RNA. B: U87MG transfected with the miRNA pool. The inner circle contains the nucleus. The outer circle defines the invasiveness.
Figure 14:
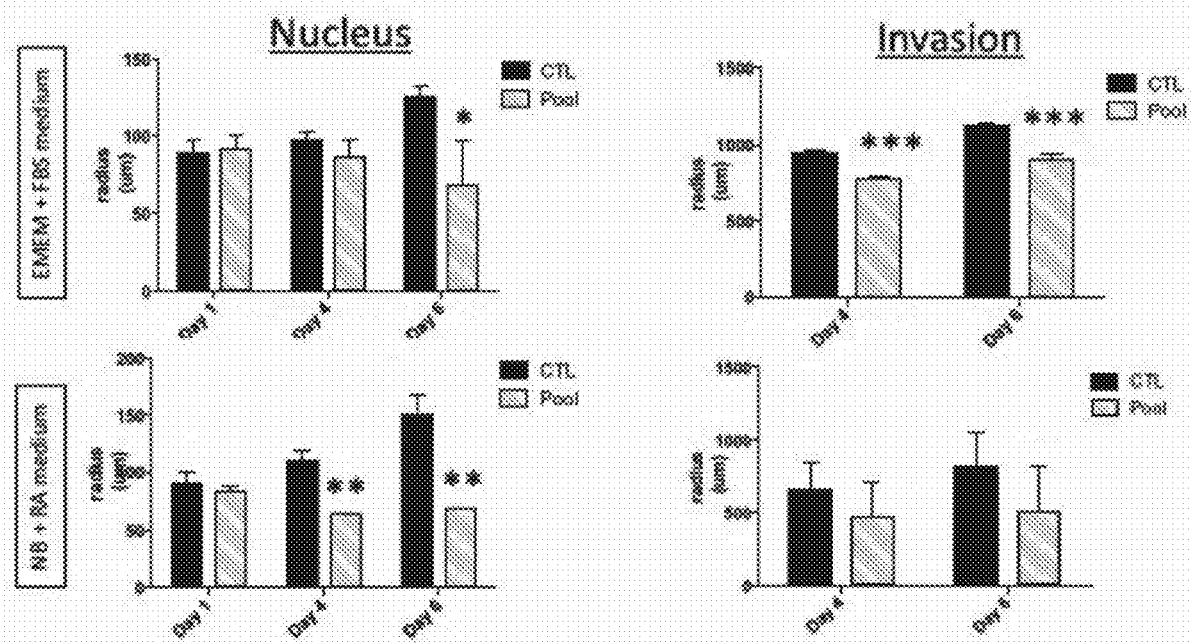

Glioblastoma U87MG spheroids were cultured in collagen gel for 6 days to test whether the miRNA pool of the invention was capable of affecting the invasiveness and growth properties thereof. As shown in FIG. 14, after a 6-day incubation, the U87MG spheroids transfected with the miRNA pool of the invention showed a significant reduction of the radius of the central nuclei in all tested conditions compared to the control spheroids (two-way ANOVA $p<0.05$ in EMEM-FBS; $p<0.01$ in NB), and also when invasiveness was measured in EMEM plus 10% FBS (two-way ANOVA $p<0.001$). These results indicate that the selected miRNA pool of the invention inhibits the proliferative and metastatic properties of the human glioblastoma U87MG cell line in vitro, marking the beginning of a new therapeutic approach for inhibiting the invasiveness of grade IV human glioblastoma.

REFERENCES

Andersson, T., Rahman, S., Sansom, S. N., Alsiö, J. M., Kaneda, M., Smith, J., O'Carroll, D., Tarakhovsky, A., and Livesey, F. J. (2010). Reversible block of mouse neural stem cell differentiation in the absence of dicer and microRNAs. PloS One 5, e13453.

Babu, H., Claasen, J.-H., Kannan, S., Rünker, A. E., Palmer, T., and Kempermann, G. (2011). A protocol for isolation and enriched monolayer cultivation of neural precursor cells from mouse dentate gyrus. Front. Neurosci. 5, 89.

Beckervordersandforth, R., Tripathi, P., Ninkovic, J., Bayam, E., Lepier, A., Stempfhuber, B., Kirchhoff, F., Hirrlinger, J., Haslinger, A., Lie, D. C., et al. (2010). In vivo fate mapping and expression analysis reveals molecular hallmarks of prospectively isolated adult neural stem cells. Cell Stem Cell 7, 744-758.

Beckervordersandforth, R., Deshpande, A., Schäffner, I., Huttner, H. B., Lepier, A., Lie, D. C., and Götz, M. (2014). In Vivo Targeting of Adult Neural Stem Cells in the Dentate Gyrus by a Split-Cre Approach. Stem Cell Rep. 2, 153-162.

Bonaguidi, M. A., Song, J., Ming, G., and Song, H. (2012). A unifying hypothesis on mammalian neural stem cell properties in the adult hippocampus. Curr. Opin. Neurobiol. 22, 754-761.

Braun, S. M. G., Machado, R. A. C., and Jessberger, S. (2013). Temporal Control of Retroviral Transgene Expression in Newborn Cells in the Adult Brain. Stem Cell Rep. 1, 114-122. Cahoy, J. D., Emery, B., Kaushal, A., Foo, L. C., Zamanian, J. L., Christopherson, K. S., Xing, Y., Lubischer, J. L., Krieg, P. A., Krupenko, S. A., et al. (2008). A transcriptome database for astrocytes, neurons, and oligodendrocytes: a new resource for understanding brain development and function. J. Neurosci. Off. J. Soc. Neurosci. 28, 264-278.

Dibajnia, P., and Morshead, C. M. (2013). Role of neural precursor cells in promoting repair following stroke. Acta Pharmacol. Sin. 34, 78-90.

Doetsch, F., Petreanu, L., Caille, I., Garcia-Verdugo, J. M., and Alvarez-Buylla, A. (2002). EGF converts transit-amplifying neurogenic precursors in the adult brain into multipotent stem cells. Neuron 36, 1021-1034.

Encinas, J. M., Vaahtokari, A., and Enikolopov, G. (2006). Fluoxetine targets early progenitor cells in the adult brain. Proc. Natl. Acad. Sci. U.S.A. 103, 8233-8238.

Encinas, J. M., Michurina, T. V., Peunova, N., Park, J.-H., Tordo, J., Peterson, D. A., Fishell, G., Koulakov, A., and Enikolopov, G. (2011). Division-coupled astrocytic differentiation and age-related depletion of neural stem cells in the adult hippocampus. Cell Stem Cell 8, 566-579.

Gage, F. H., and Temple, S. (2013). Neural stem cells: generating and regenerating the brain. Neuron 80, 588-601.

Gargaro, A. C., Sakamoto, A. C., Bianchin, M. M., Geraldi, C. de V. L., Scorsi-Rosset, S., Coimbra, E. R., Carlotti, C. G., Assirati, J. A., and Velasco, T. R. (2013). Atypical neuropsychological profiles and cognitive outcome in mesial temporal lobe epilepsy. Epilepsy Behav. EB 27, 461-469.

Gibbons, M. B., Smeal, R. M., Takahashi, D. K., Vargas, J. R., and Wilcox, K. S. (2013). Contributions of astrocytes to epileptogenesis following status epilepticus: opportunities for preventive therapy? Neurochem. Int. 63, 660-669.

Gleeson, J. G., Lin, P. T., Flanagan, L. A., and Walsh, C. A. (1999). Doublecortin is a microtubule-associated protein and is expressed widely by migrating neurons. Neuron 23, 257-271.

Heuser, K., Taubøll, E., Nagelhus, E. A., Cvancarova, M., Petter Ottersen, O., and Gjerstad, L. (2009). Phenotypic characteristics of temporal lobe epilepsy: the impact of hippocampal sclerosis. Acta Neurol. Scand. Suppl. 8-13.

Kempermann, G. (2011). The pessimist's and optimist's views of adult neurogenesis. Cell 145, 1009-1011.

Leker, R. R., Lasri, V., and Chernoguz, D. (2009). Growth factors improve neurogenesis and outcome after focal cerebral ischemia. J. Neural Transm. Vienna Austria 1996 116, 1397-1402.

Madisen, L., Zwingman, T. A., Sunkin, S. M., Oh, S. W., Zariwala, H. A., Gu, H., Ng, L. L., Palmiter, R. D., Hawrylycz, M. J., Jones, A. R., et al. (2010). A robust and high-throughput Cre reporting and characterization system for the whole mouse brain. Nat. Neurosci. 13, 133-140.

Malberg, J. E., Eisch, A. J., Nestler, E. J., and Duman, R. S. (2000). Chronic antidepressant treatment increases neurogenesis in adult rat hippocampus. J. Neurosci. Off. J. Soc. Neurosci. 20, 9104-9110.

Marlatt, M. W., and Lucassen, P. J. (2010). Neurogenesis and Alzheimer's disease: Biology and pathophysiology in mice and men. Curr. Alzheimer Res. 7, 113-125.

Mullen, R. J., Buck, C. R., and Smith, A. M. (1992). NeuN, a neuronal specific nuclear protein in vertebrates. Dev. Camb. Engl. 116, 201-211.

Murchison, E. P., Partridge, J. F., Tam, O. H., Cheloufi, S., and Hannon, G. J. (2005). Characterization of Dicer-deficient murine embryonic stem cells. Proc. Natl. Acad. Sci. U.S.A. 102, 12135-12140.

Pons-Espinal, M., De Lagran, M. M., and Dierssen, M. (2013). Functional implications of hippocampal adult neurogenesis in intellectual disabilities.

Santarelli, L., Saxe, M., Gross, C., Surget, A., Battaglia, F., Dulawa, S., Weisstaub, N., Lee, J., Duman, R., Arancio, O., et al. (2003). Requirement of hippocampal neurogenesis for the behavioral effects of antidepressants. Science 301, 805-809.

Schouten, M., Buijink, M. R., Lucassen, P. J., and Fitzsimons, C. P. (2012). New Neurons in Aging Brains: Molecular Control by Small Non-Coding RNAs. Front. Neurosci. 6, 25.

Shimada, I. S., LeComte, M. D., Granger, J. C., Quinlan, N. J., and Spees, J. L. (2012). Selfrenewal and differentiation of reactive astrocyte-derived neural stem/progenitor cells isolated from the cortical peri-infarct area after stroke. J. Neurosci. Off. J. Soc. Neurosci. 32, 7926-7940.

Sierra, A., Martin-Suarez, S., Valcárcel-Martin, R., Pascual-Brazo, J., Aelvoet, S.-A., Abiega, O., Deudero, J. J., Brewster, A. L., Bernales, I., Anderson, A. E., et al. (2015). Neuronal hyperactivity accelerates depletion of neural stem cells and impairs hippocampal neurogenesis. Cell Stem Cell 16, 488-503.

Walker, T. L., and Kempermann, G. (2014). One mouse, two cultures: isolation and culture of adult neural stem cells from the two neurogenic zones of individual mice. J. Vis. Exp. JoVE e51225.

Wang, F., Hao, H., Zhao, S., Zhang, Y., Liu, Q., Liu, H., Liu, S., Yuan, Q., Bing, L., Ling, E.-A., et al. (2011). Roles of activated astrocyte in neural stem cell proliferation and differentiation. Stem Cell Res. 7, 41-53.

The invention claimed is:

1. A pharmaceutical composition comprising a plurality of microRNAs and a pharmaceutically acceptable carrier and/or diluent and/or excipient, said plurality of micro mRNAs comprising a microRNA comprising nucleotides 1-8 of SEQ ID NO:1, a microRNA comprising nucleotides 2-11 of SEQ ID NO:2, a microRNA comprising nucleotides 2-11 of SEQ ID NO:3, a microRNA comprising nucleotides 2-8 of SEQ ID NO:4, a microRNA comprising nucleotides 2-11 of SEQ ID NO:5, a microRNA comprising nucleotides 2-8 of SEQ ID NO:6, a microRNA comprising nucleotides 2-11 of SEQ ID NO:7, a microRNA comprising nucleotides 2-11 of SEQ ID NO:8, a microRNA comprising nucleotides 2-11 of SEQ ID NO:9, a microRNA comprising nucleotides 2-11 of SEQ ID NO:10 and a microRNA comprising nucleotides 2-11 of SEQ ID NO:11, wherein the nucleotide positions are indicated with reference to the 5' terminus of the sequence.

2. The pharmaceutical composition of claim 1, comprising the following microRNAs:
   hsa-miR-124-3p MIMAT0000422 (SEQ ID NO:1);
   hsa-miR-127-3p MIMAT0000446 (SEQ ID NO:2);
   hsa-miR-134-5p MIMAT0000447 (SEQ ID NO:3);
   hsa-miR-135a-5p MIMAT0000428 (SEQ ID NO:4);
   hsa-miR-139-5p MIMAT0000250 (SEQ ID NO:5);
   hsa-miR-218-5p MIMAT0000275 (SEQ ID NO:6);
   hsa-miR-370-3p MIMAT0000722 (SEQ ID NO:7);
   hsa-miR-376b-3p MIMAT0002172 (SEQ ID NO:8);
   hsa-miR-382-5p MIMAT0000737 (SEQ ID NO:9);
   hsa-miR-411-5p MIMAT0003329 (SEQ ID NO:10); and
   hsa-miR-708-5p MIMAT0004926 (SEQ ID NO:11).

3. A method of promoting, stimulating or increasing neuronal differentiation in a subject in need thereof, comprising administering to the subject a pharmaceutical composition of claim 1.

4. The method of claim 3, wherein the subject is affected by a condition selected from one or more of a neurodegenerative disease, an age-related neurodegenerative condition, a neurodegeneration-related cognitive decline, or a tumour disease of nervous tissue, and a damage to nervous tissue caused by epilepsy and/or stroke.

5. The method of claim 3, wherein the tumour disease of nervous tissue is a glioblastoma.

6. The method of claim 3, wherein the subject is a human being.

7. A method of stimulating neurogenesis in a subject in need thereof, comprising administering to the subject a pharmaceutical composition of claim 1.

8. The method of claim 7, wherein the subject suffers from depression.

9. The method of claim 7, wherein the subject is a human being.

10. A kit comprising a plurality of microRNAs and a pharmaceutically acceptable carrier and/or diluent and/or excipient, said plurality of micro mRNAs comprising: a microRNA comprising the seed sequence SEQ ID NO:12, a microRNA comprising the seed sequence SEQ ID NO:13, a microRNA comprising the seed sequence SEQ ID NO:14, a microRNA comprising the seed sequence SEQ ID NO:15, a microRNA comprising the seed sequence SEQ ID NO:16, a microRNA comprising the seed sequence SEQ ID NO:17, a microRNA comprising the seed sequence SEQ ID NO:18, a microRNA comprising the seed sequence SEQ ID NO:19, a microRNA comprising the seed sequence SEQ ID NO:20, a microRNA comprising the seed sequence SEQ ID NO:21 and a microRNA comprising the seed sequence SEQ ID NO:22.

11. The kit of claim 10, wherein the plurality of microRNAs includes the following microRNAs:

hsa-miR-124-3p MIMAT0000422 (SEQ ID NO:1);
hsa-miR-127-3p MIMAT0000446 (SEQ ID NO:2);
hsa-miR-134-5p MIMAT0000447 (SEQ ID NO:3);
hsa-miR-135a-5p MIMAT0000428 (SEQ ID NO:4);
hsa-miR-139-5p MIMAT0000250 (SEQ ID NO:5);
hsa-miR-218-5p MIMAT0000275 (SEQ ID NO:6);
hsa-miR-370-3p MIMAT0000722 (SEQ ID NO:7);
hsa-miR-376b-3p MIMAT0002172 (SEQ ID NO:8);
hsa-miR-382-5p MIMAT0000737 (SEQ ID NO:9);
hsa-miR-411-5p MIMAT0003329 (SEQ ID NO:10); and
hsa-miR-708-5p MIMAT0004926 (SEQ ID NO:11).

12. A method of promoting, stimulating or increasing neuronal differentiation in a subject in need thereof, comprising administering to the subject the plurality of microRNAs of claim 10, wherein the microRNAs in said plurality of microRNAs are simultaneously, separately or sequentially administered to the subject.

13. The method of claim 12, wherein the subject is affected by a condition selected from one or more of a neurodegenerative disease, an age-related neuro-degenerative condition, or a neurodegeneration-related cognitive decline, a tumour disease of nervous tissue, and a damage to nervous tissue caused by epilepsy and/or stroke.

14. The method of claim 13, wherein the tumour disease of nervous tissue is a glioblastoma.

15. The method of claim 12, wherein the subject is a human being.

16. A method of stimulating neurogenesis in a subject in need thereof, comprising administering to the subject the plurality of microRNAs of claim 10, wherein the microRNAs in said plurality of microRNAs are simultaneously, separately or sequentially administered to the subject.

17. The method of claim 16, wherein the subject suffers from depression.

18. The method of claim 16, wherein the subject is a human being.

* * * * *